(12) United States Patent
Worthington et al.

(10) Patent No.: US 10,799,257 B2
(45) Date of Patent: Oct. 13, 2020

(54) SEAL FOR SURGICAL INSTRUMENT

(71) Applicant: ETHICON LLC, Guaynabo, PR (US)

(72) Inventors: Sarah A. Worthington, Maineville, OH (US); Andrew Kolpitcke, Centerville, OH (US); Laura A. Schoettmer, Cincinnati, OH (US); Laura R. Corsetto, West Orange, NJ (US); John E. Brady, Liberty Township, OH (US); Christopher J. Hess, Blue Ash, OH (US); Douglas E. Withers, Cincinnati, OH (US); Ryan P. Posey, Cincinnati, OH (US); Jeffery D. Bruns, Cincinnati, OH (US); Gregory G. Scott, Cincinnati, OH (US); Alexander R. Cuti, Cincinnati, OH (US); Gregory J. Bakos, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 294 days.

(21) Appl. No.: 15/934,148

(22) Filed: Mar. 23, 2018

(65) Prior Publication Data

US 2019/0290308 A1     Sep. 26, 2019

(51) Int. Cl.
*A61B 17/29* (2006.01)
*A61B 17/072* (2006.01)
*A61B 17/00* (2006.01)

(52) U.S. Cl.
CPC .......... *A61B 17/29* (2013.01); *A61B 17/072* (2013.01); *A61B 2017/00367* (2013.01);
(Continued)

(58) Field of Classification Search
CPC ............ A61B 17/29; A61B 17/02; A61B 2017/00367; A61B 2017/0734;
(Continued)

(56) References Cited

U.S. PATENT DOCUMENTS 5,792,135 A    8/1998  Madhani et al.
5,817,084 A    10/1998 Jensen
(Continued)

FOREIGN PATENT DOCUMENTS

EP      2 839 797 A2     2/2015
WO   WO 2015/153642 A1   10/2015

OTHER PUBLICATIONS

Hollister, S., "Waterproofing explained: How Apple, Samsung and Sony keep the liquid out," cnet.com, Sep. 21, 2016, downloaded from https://www.cnet.com/news/how-does-waterproofing-work-apple-iphone-7-samsung-galaxy-s7-sony-xperia/, copyrighted by CBS Interactive Inc., 8 pgs.

(Continued)

*Primary Examiner* — Erich G. Herbermann
(74) *Attorney, Agent, or Firm* — Frost Brown Todd LLC

(57) ABSTRACT

A surgical instrument includes a body assembly, a shaft assembly that releasably attaches to the body assembly, and an end effector at a distal end of the shaft assembly. The body assembly includes a first electrical contact and a first sealing portion. The shaft assembly includes a second electrical contact and a second sealing portion. The first and second electrical contacts are configured to electrically couple together to establish an electrical connection therebetween when the shaft assembly is attached to the body assembly. The first and second sealing portions are configured to sealingly engage one another when the shaft assembly is attached to the body assembly to establish a liquid-tight seal that surrounds the electrical connection.

18 Claims, 27 Drawing Sheets

(52) U.S. Cl.
CPC .............. *A61B 2017/00734* (2013.01); *A61B 2017/07257* (2013.01); *A61B 2017/07271* (2013.01); *A61B 2017/07285* (2013.01); *A61B 2017/291* (2013.01); *A61B 2017/2901* (2013.01); *A61B 2017/2946* (2013.01); *A61B 2017/2948* (2013.01)

(58) Field of Classification Search
CPC .......... A61B 2017/07257; A61B 2017/07271; A61B 2017/07285; A61B 17/2901; A61B 2017/291; A61B 2017/2946; A61B 2017/2948; H01R 3/00; H01R 12/00; H01R 9/00; H01R 9/03; H01R 9/11; H01R 9/15; H01R 9/16; H01R 9/22
See application file for complete search history.

(56) References Cited

U.S. PATENT DOCUMENTS

| | | | |
|---|---|---|---|
| 5,817,093 A | 10/1998 | Williamson, IV et al. | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 7,404,508 B2 | 7/2008 | Smith et al. | |
| 7,524,320 B2 | 4/2009 | Tierney et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,608,045 B2 | 12/2013 | Smith et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 8,991,678 B2 | 3/2015 | Wellman et al. | |
| 9,072,535 B2 | 7/2015 | Shelton, IV et al. | |
| 9,186,142 B2 | 11/2015 | Fanelli et al. | |
| 9,301,759 B2 | 4/2016 | Spivey et al. | |
| 9,345,481 B2 | 5/2016 | Hall et al. | |
| 9,724,094 B2 | 8/2017 | Baber et al. | |
| 9,795,379 B2 | 10/2017 | Leimbach et al. | |
| 9,839,425 B2 | 12/2017 | Zergiebel et al. | |
| 9,913,642 B2 | 3/2018 | Leimbach et al. | |
| 2014/0263541 A1 | 9/2014 | Leimbach et al. | |
| 2014/0263552 A1 | 9/2014 | Hall et al. | |
| 2015/0374353 A1* | 12/2015 | Zergiebel | A61B 17/07207 403/376 |
| 2016/0066911 A1 | 3/2016 | Baber et al. | |
| 2016/0066914 A1* | 3/2016 | Baber | H02H 3/207 227/180.1 |
| 2016/0310134 A1 | 10/2016 | Contini et al. | |

OTHER PUBLICATIONS

U.S. Appl. No. 15/635,663, filed Jun. 28, 2017.
U.S. Appl. No. 15/635,631, filed Jun. 28, 2017.
U.S. Appl. No. 15/635,837, filed Jun. 28, 2017.
U.S. Appl. No. 15/636,096, filed Jun. 28, 2017.
U.S. Appl. No. 15/934,139, filed Mar. 23, 2018.
U.S. Appl. No. 15/934,160, filed Mar. 23, 2018.
U.S. Appl. No. 15/934,166, filed Mar. 23, 2018.
U.S. Appl. No. 15/934,173, filed Mar. 23, 2018.
U.S. Appl. No. 15/934,180, filed Mar. 23, 2018.
U.S. Appl. No. 15/934,190, filed Mar. 23, 2018.

* cited by examiner

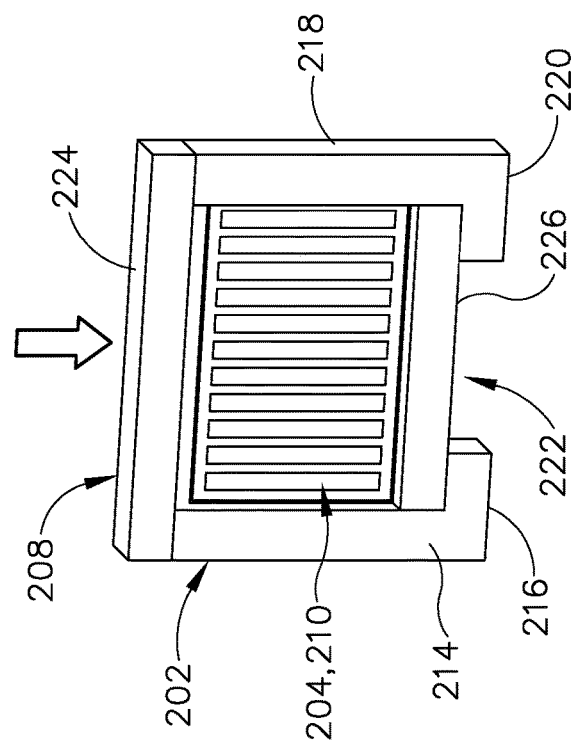
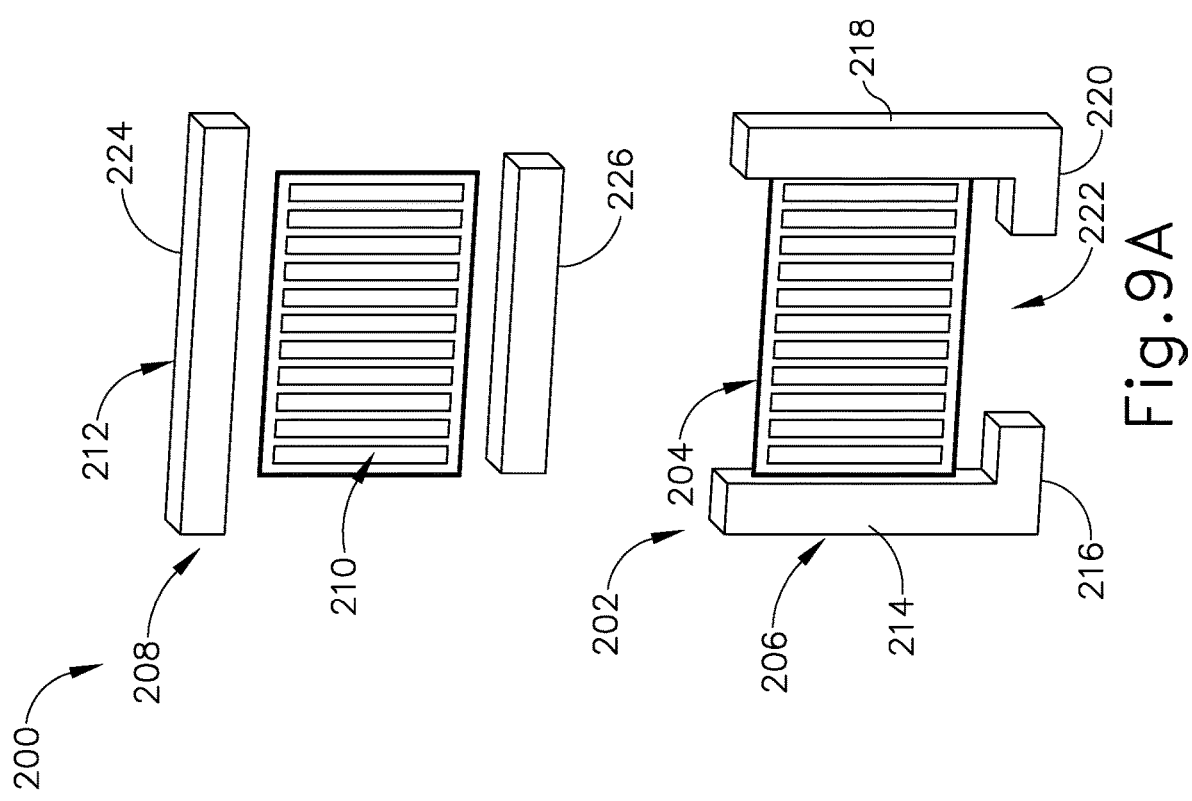
Fig.9A
Fig.9B

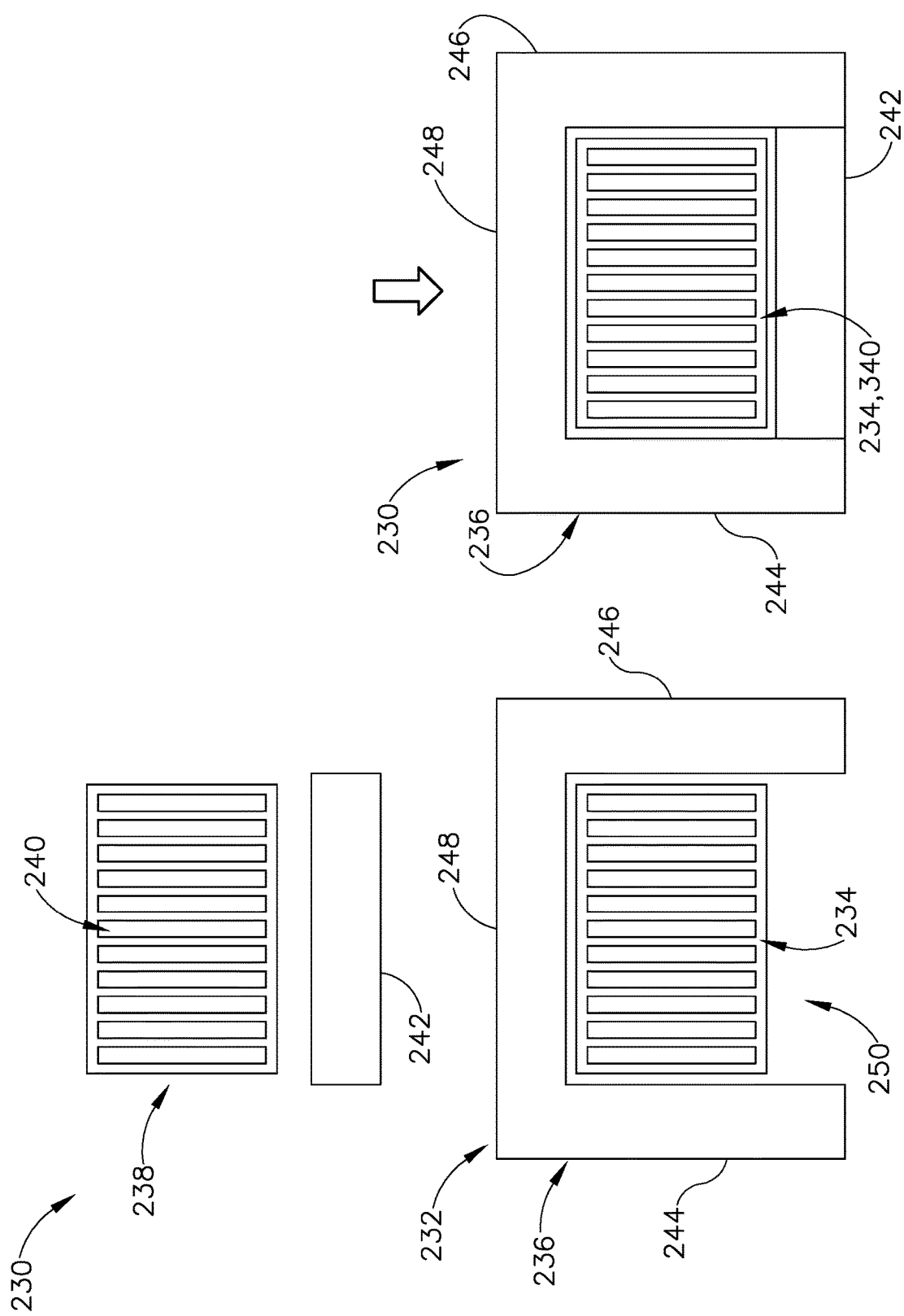

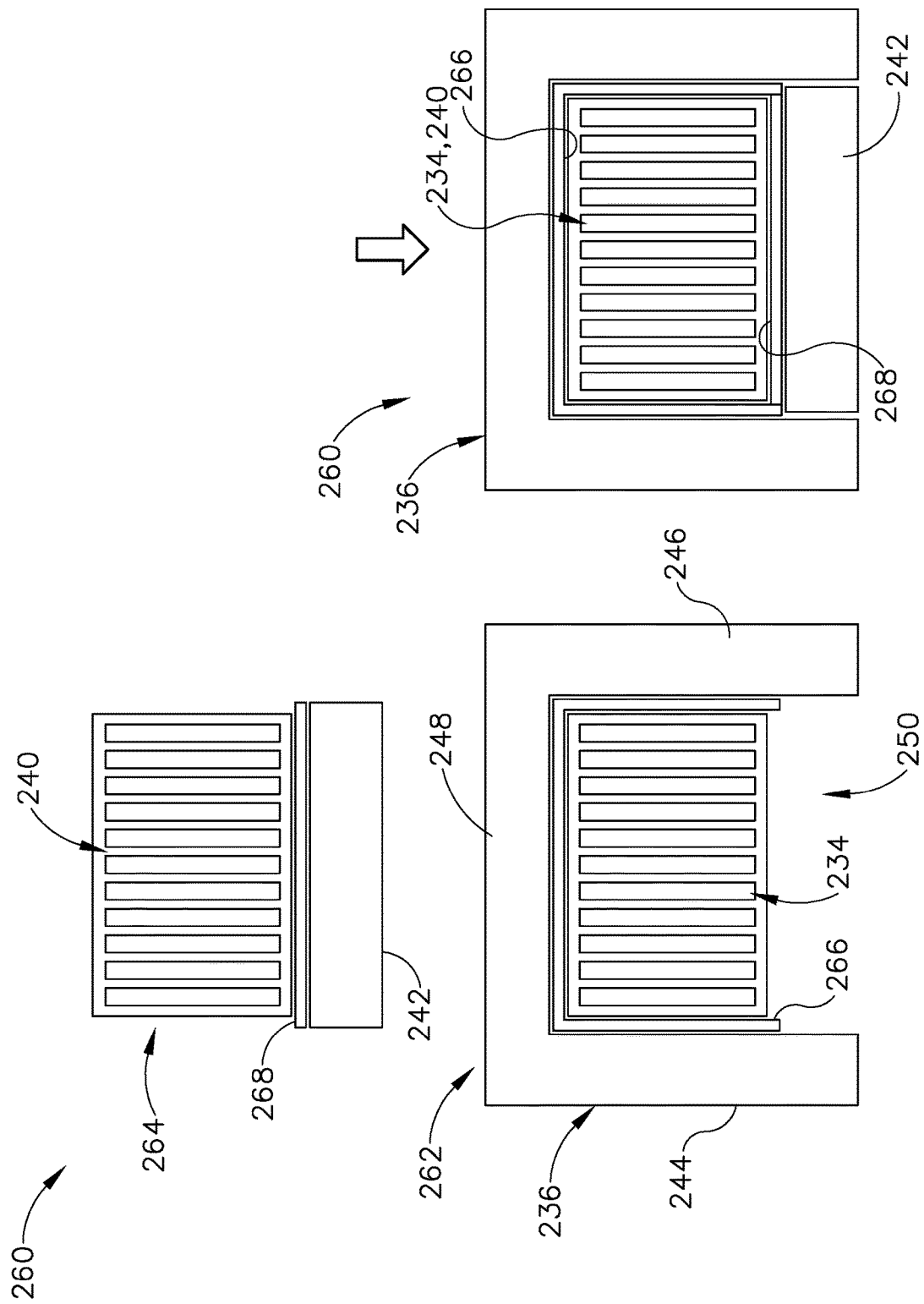

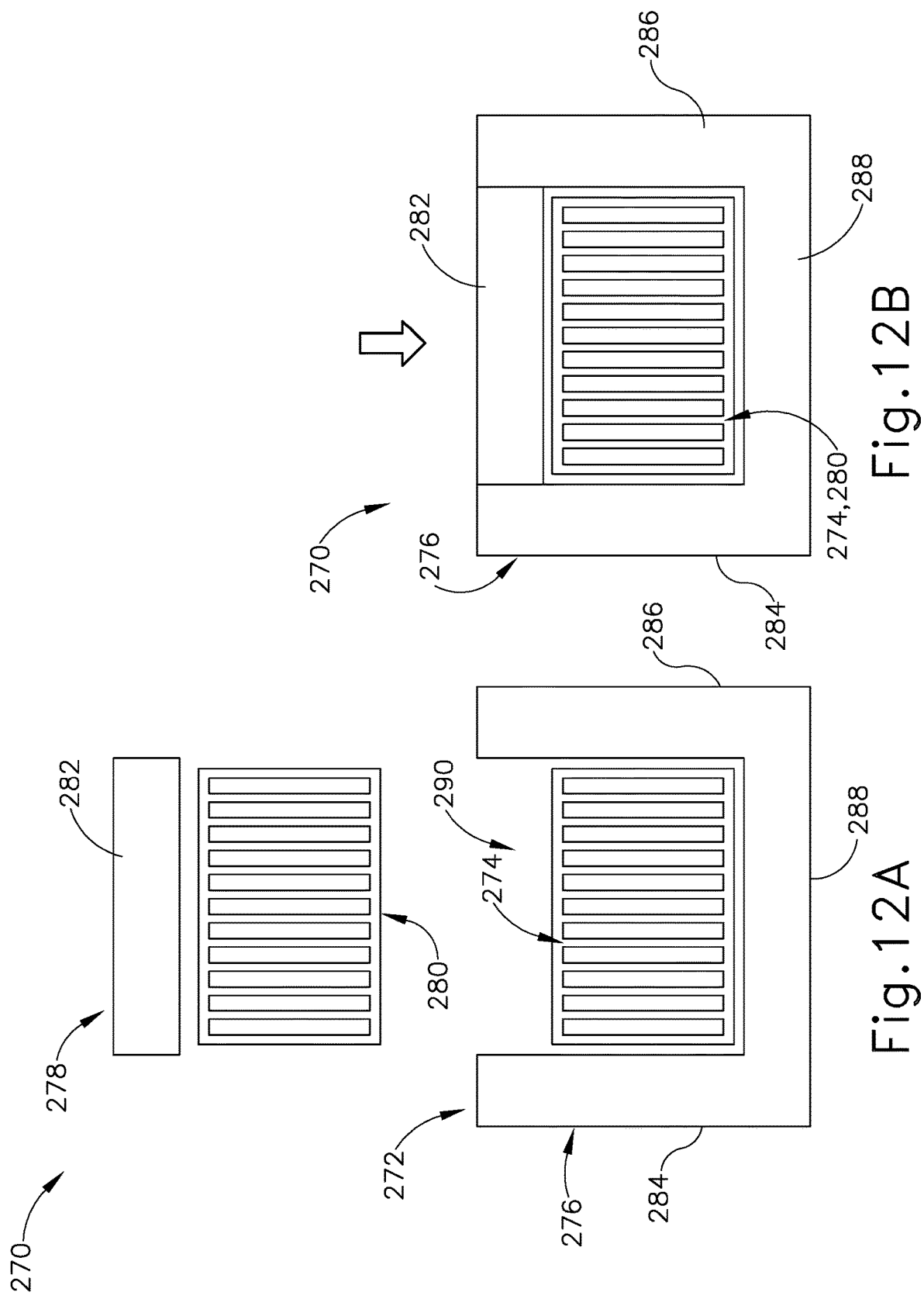

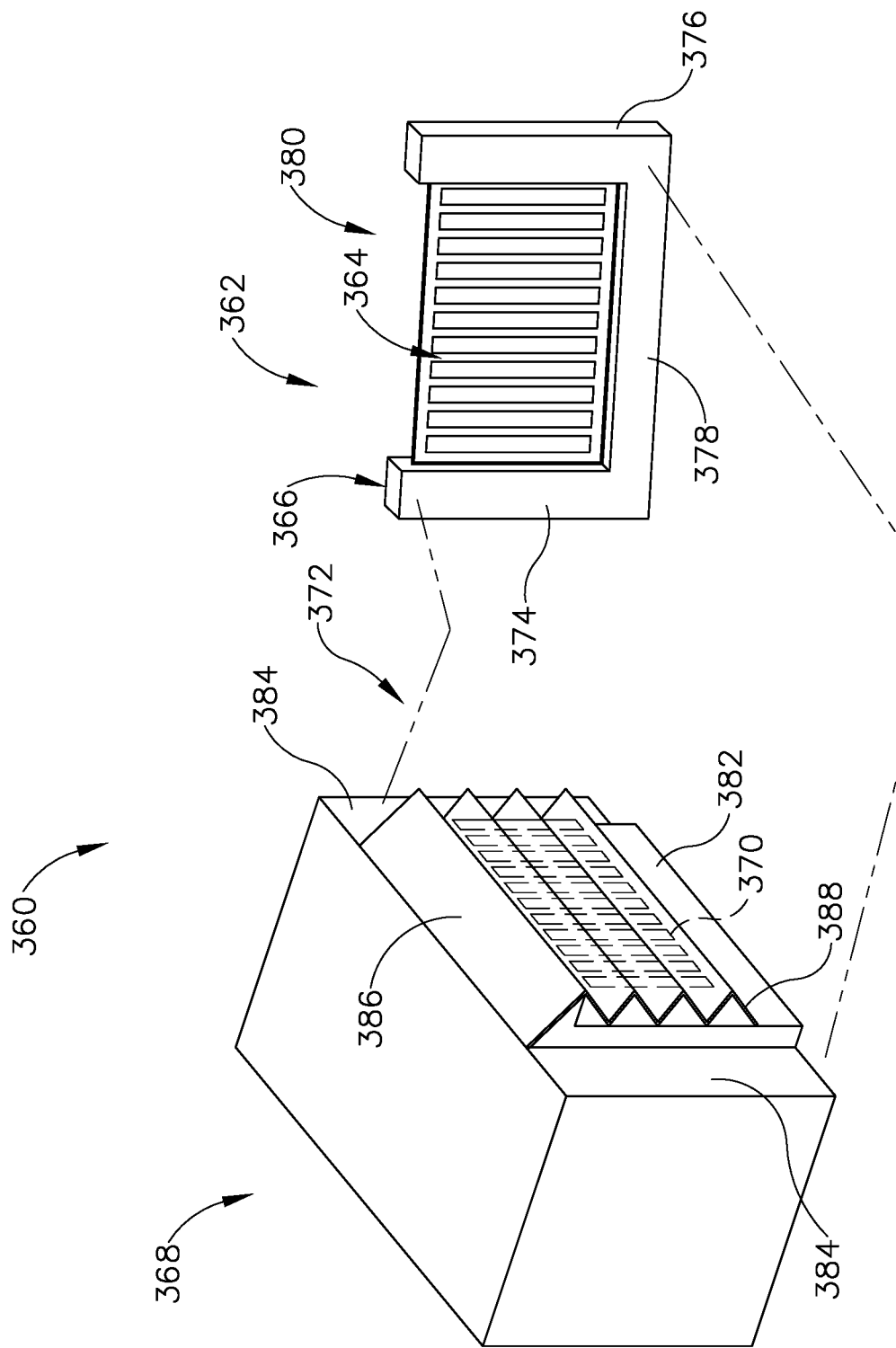

SEAL FOR SURGICAL INSTRUMENT

BACKGROUND

Endoscopic surgical instruments may be preferred over traditional open surgical devices in certain instances to create a smaller surgical incision in the patient and thereby reduce the post-operative recovery time and complications. Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,404,508, entitled "Surgical Stapling and Cutting Device," issued Jul. 29, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued Nov. 17, 2015; and U.S. Pat. No. 9,795,379, entitled "Surgical Instrument with Multi-Diameter Shaft," issued Oct. 24, 2017. The disclosure of each of the above-cited U.S. patents is incorporated by reference herein.

While the surgical staplers referred to above are described as being used in endoscopic procedures, such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Of course, surgical staplers may be used in various other settings and procedures.

While several surgical instruments and systems have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 9A depicts a schematic perspective view of an exemplary sealable electrical connection assembly suitable for use with the surgical instrument of FIG. 1, showing first and second portions of the assembly in a disengaged state;

FIG. 9B depicts a schematic perspective view of the sealable electrical connection assembly of FIG. 9A, showing the first and second portions of the assembly in an engaged state;

FIG. 10A depicts a schematic front elevational view of another exemplary sealable electrical connection assembly suitable for use with the surgical instrument of FIG. 1, showing the first and second portions of the assembly in a disengaged state;

FIG. 10B depicts a schematic front elevational view of the exemplary sealable electrical connection assembly of FIG. 10A, showing the first and second portions of the assembly in an engaged state;

FIG. 11A depicts a schematic front elevational view of another exemplary sealable electrical connection assembly suitable for use with the surgical instrument of FIG. 1, showing the first and second portions of the assembly in a disengaged state;

FIG. 11B depicts a schematic front elevational view of the exemplary sealable electrical connection assembly of FIG. 11A, showing the first and second portions of the assembly in an engaged state;

FIG. 12A depicts a schematic front elevational view of another exemplary sealable electrical connection assembly suitable for use with the surgical instrument of FIG. 1, showing the first and second portions of the assembly in a disengaged state;

FIG. 12B depicts a schematic front elevational view of the exemplary sealable electrical connection assembly of FIG. 12A, showing the first and second portions of the assembly in an engaged state;

FIG. 16 depicts a schematic perspective view of another exemplary sealable electrical connection assembly suitable for use with the surgical instrument of FIG. 1, showing the first and second portions of the assembly in a disengaged state;

Figure 1:
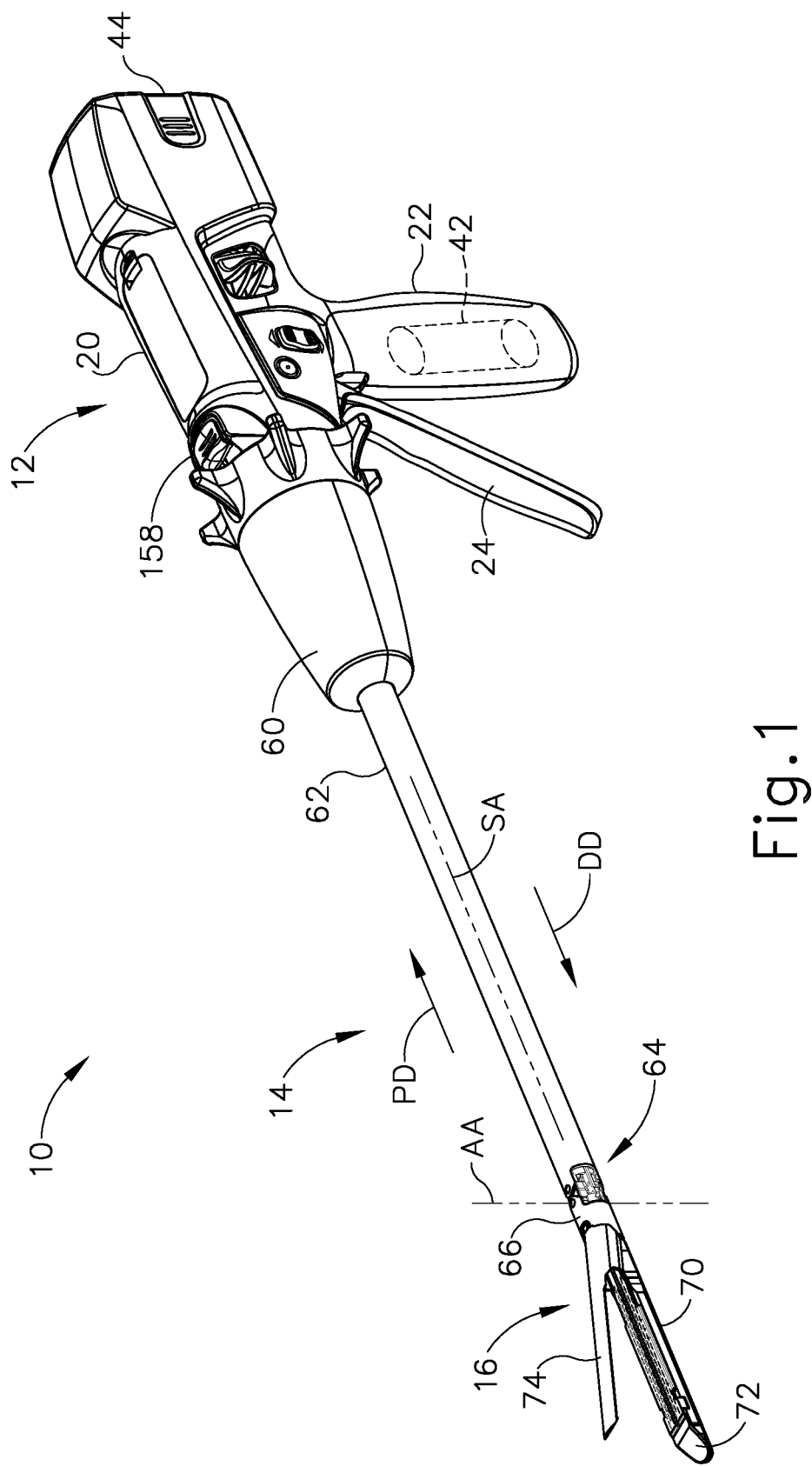
FIG. 1 depicts a perspective view of an exemplary surgical instrument having a handle assembly and an interchangeable shaft assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, clinician, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Surgical Stapling Instrument

Figure 2:
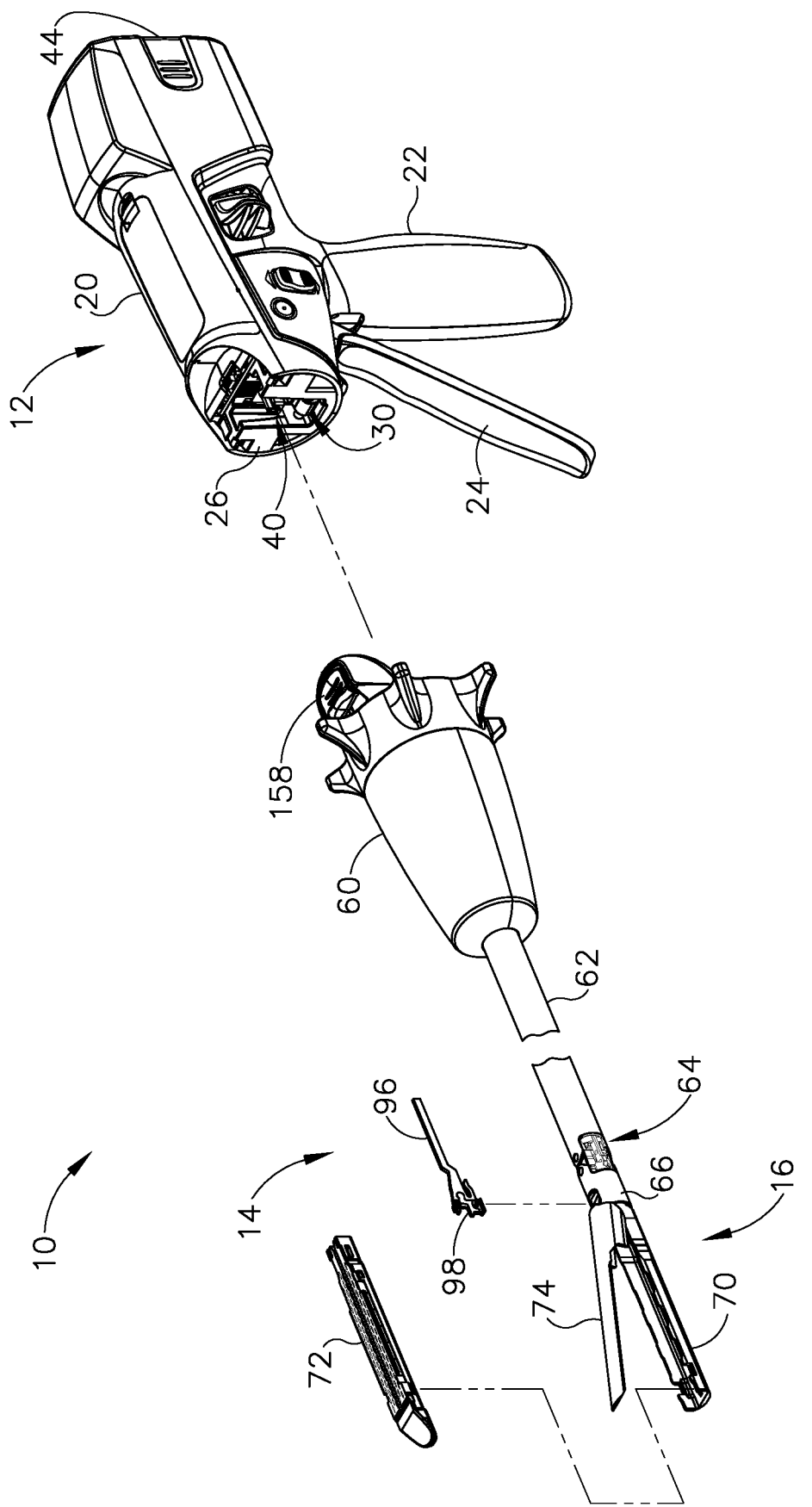
FIG. 2 depicts a partially exploded perspective view of the surgical instrument of FIG. 1, showing the interchangeable shaft assembly separated from the handle assembly.

FIGS. 1-2 show a motor-driven surgical instrument (10) suitable for use in a variety of surgical procedures. In the illustrated example, instrument (10) includes a handle assembly (12) and an interchangeable shaft assembly (14) releasably coupled to and extending distally from handle assembly (12). Interchangeable shaft assembly (14) includes a surgical end effector (16) arranged at a distal end thereof, and which is configured to perform one or more surgical tasks or procedures. In some applications, interchangeable shaft assembly (14) may be effectively employed with a tool drive assembly of a robotically controlled or automated surgical system. For example, interchangeable shaft assembly (14) may be employed with various robotic systems, instruments, components, and methods such as those disclosed in U.S. Pat. No. 9,072,535, entitled "Surgical Stapling Instruments With Rotatable Staple Deployment Arrangements," issued Jul. 7, 2015, the disclosure of which is incorporated by reference herein.

A. Handle Assembly of Surgical Stapling Instrument

Handle assembly (12) comprises a body (20) that includes a pistol grip (22) configured to be grasped by a clinician, and a closure trigger (24) configured to pivot toward and away from pistol grip (22) to selectively close and open end effector (16), as described in greater detail below. In the present example, end effector (16) is configured to cut and staple tissue captured by end effector (16). In other examples, end effector (16) may be configured to treat tissue via application of various other types of movements and energies, such as radio frequency (RF) energy and/or ultrasonic energy, for example.

Figure 3A:
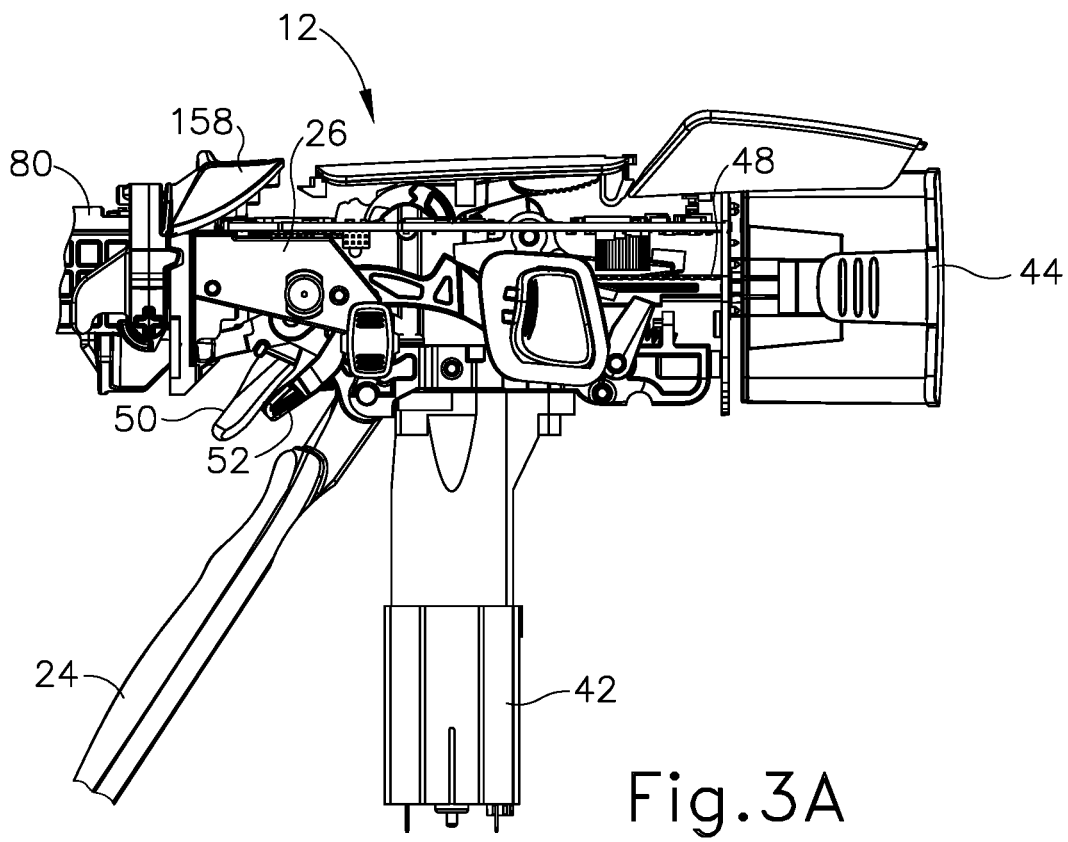
FIG. 3A depicts a side elevational view of the surgical instrument of FIG. 1, with a body of the handle assembly omitted, showing a closure trigger of the handle assembly in an unactuated position.
Figure 3B:
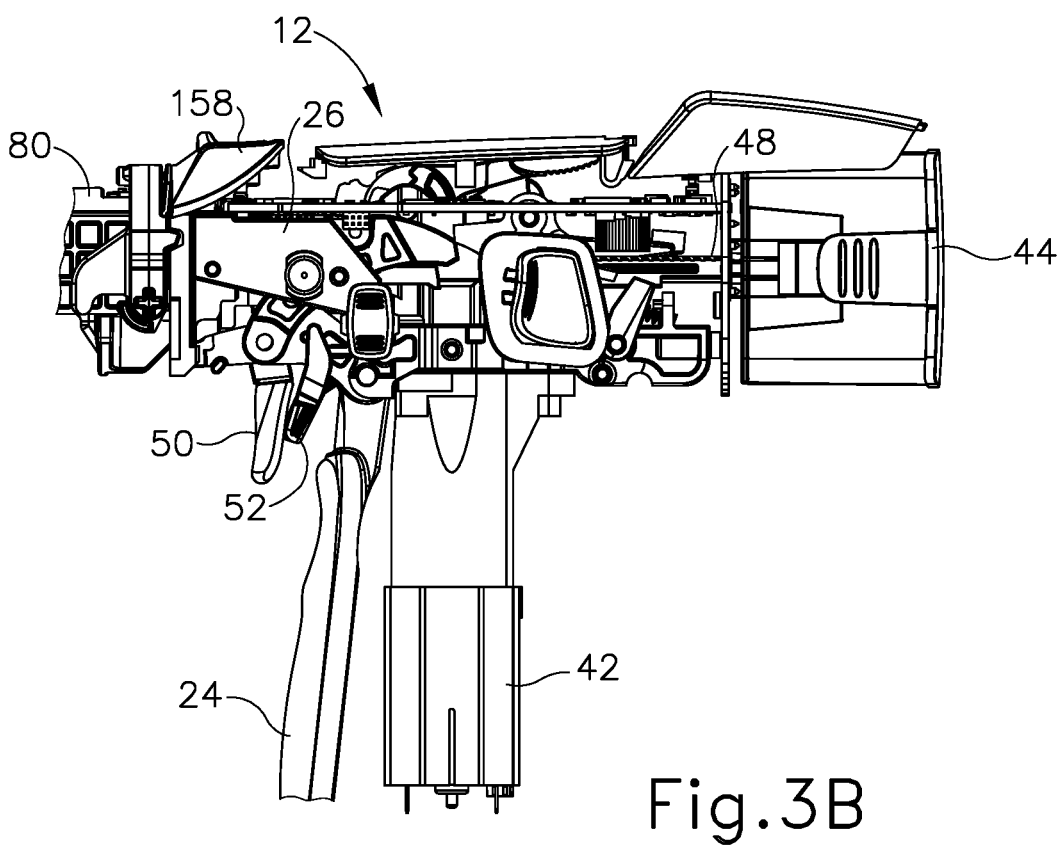
FIG. 3B depicts a side elevational view of the surgical instrument of FIG. 1, with a body of the handle assembly omitted, showing a closure trigger of the handle assembly in an actuated position.
Figure 4:
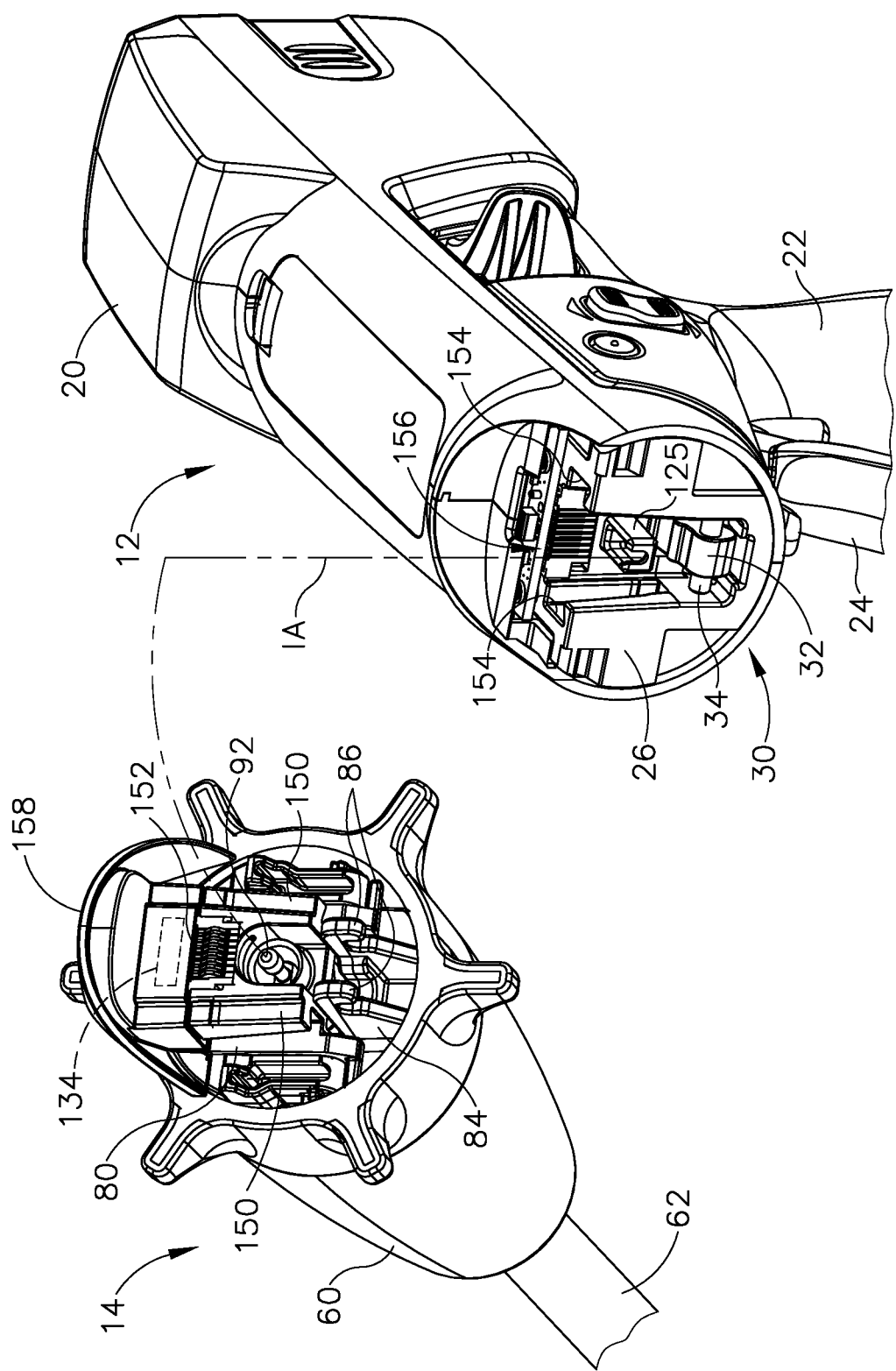
FIG. 4 depicts another perspective view of the surgical instrument of FIG. 1 in a separated state, showing additional details of a distal end of the handle assembly and a mating proximal end of the interchangeable shaft assembly.

As seen in FIGS. 2-4, handle assembly body (20) houses a support structure in the form of a handle frame (26) that supports a plurality of drive systems configured to generate and apply various control motions to corresponding portions of interchangeable shaft assembly (14). In particular, handle frame (26) supports a first drive system in the form of a closure drive system (30) that is operable to selectively close and open end effector (16) to thereby capture and release tissue. Closure drive system (30) includes an actuator in the form of closure trigger (24), which is pivotally supported by handle frame (26) and is operatively coupled with end effector (16) via components of shaft assembly (14) described below. Closure trigger (24) is configured to be squeezed by a clinician toward pistol grip (22) from an unactuated position (FIG. 3A) that provides end effector (16) in an open state for releasing tissue, to an actuated position (FIG. 3B) that provides end effector (16) in a closed state for clamping tissue. Closure trigger (24) may be biased toward the unactuated position by a resilient member (not shown). As seen best in FIG. 4, closure drive system (30) further comprises a linkage assembly that couples closure trigger (24) with end effector (16). The linkage assembly includes a closure link (32) and a transversely extending attachment pin (34) coupled to a distal end of closure link (32). Attachment pin (34) and the distal end of closure link (32) are accessible through a distal opening in handle assembly (12).

Handle assembly body (20) further supports a second drive system in the form of a firing drive system (40) configured to apply firing motions to corresponding portions of interchangeable shaft assembly (14) and its end effector (16). In the present example, firing drive system (40) employs an electric motor (42) that is housed within pistol grip (22) of handle assembly (12) and is operatively coupled with end effector (16), as described below. Electric motor (42) may be of any suitable type, such as a DC brushed motor, a brushless motor, a cordless motor, a synchronous motor, a stepper motor, or any other suitable type of electric motor. Electric motor (42) is powered by a power source shown in the form of a power pack (44) removably coupled to a proximal portion of handle assembly body (20). Power pack (44) includes one or more batteries (not shown) of any suitable type, and may be rechargeable or replaceable.

As seen in FIG. 4, electric motor (42) is electrically coupled to and controlled by a circuit board (46) supported by handle frame (26) within handle assembly body (20). Circuit board (46) may include a microcontroller and is configured to direct power from power pack (44) to electric motor (42) and thereby energize motor (42) to fire end effector (16). Electric motor (42) is configured to interface with a drive gear arrangement (not shown) that is operable to actuate an elongate drive member (48) axially relative to handle frame (26) in response to activation of motor (42). As seen best in FIG. 5, a distal end of drive member (48) is exposed through a distal opening of handle assembly (12) and is configured to couple to a translating member of shaft assembly (14) to thereby operatively couple motor (42) with end effector (16), as described below.

Electric motor (42) is energized by battery pack (44) in response to actuation of a firing trigger (50), which is pivotally supported by handle assembly (12) as best seen in FIGS. 3A and 3B. In the present example, firing trigger (50) is positioned "outboard" of closure trigger (24). Similar to closure trigger (24), firing trigger (50) is configured to be squeezed by the clinician toward pistol grip (22) from an unactuated position (FIG. 3B) to an actuated position (not shown). Firing trigger (50) may be biased toward the unactuated position by a resilient member (not shown). When firing trigger (50) is depressed from the unactuated position to the actuated position, firing trigger (50) causes battery pack (44) to energize motor (42) to actuate drive member (48) longitudinally and thereby fire end effector (16). As shown in FIGS. 3A and 3B, handle assembly (12) further includes a firing trigger safety button (52) that is selectively pivotable between a safety position and a firing position to prevent inadvertent actuation of firing trigger (50).

Figure 5:
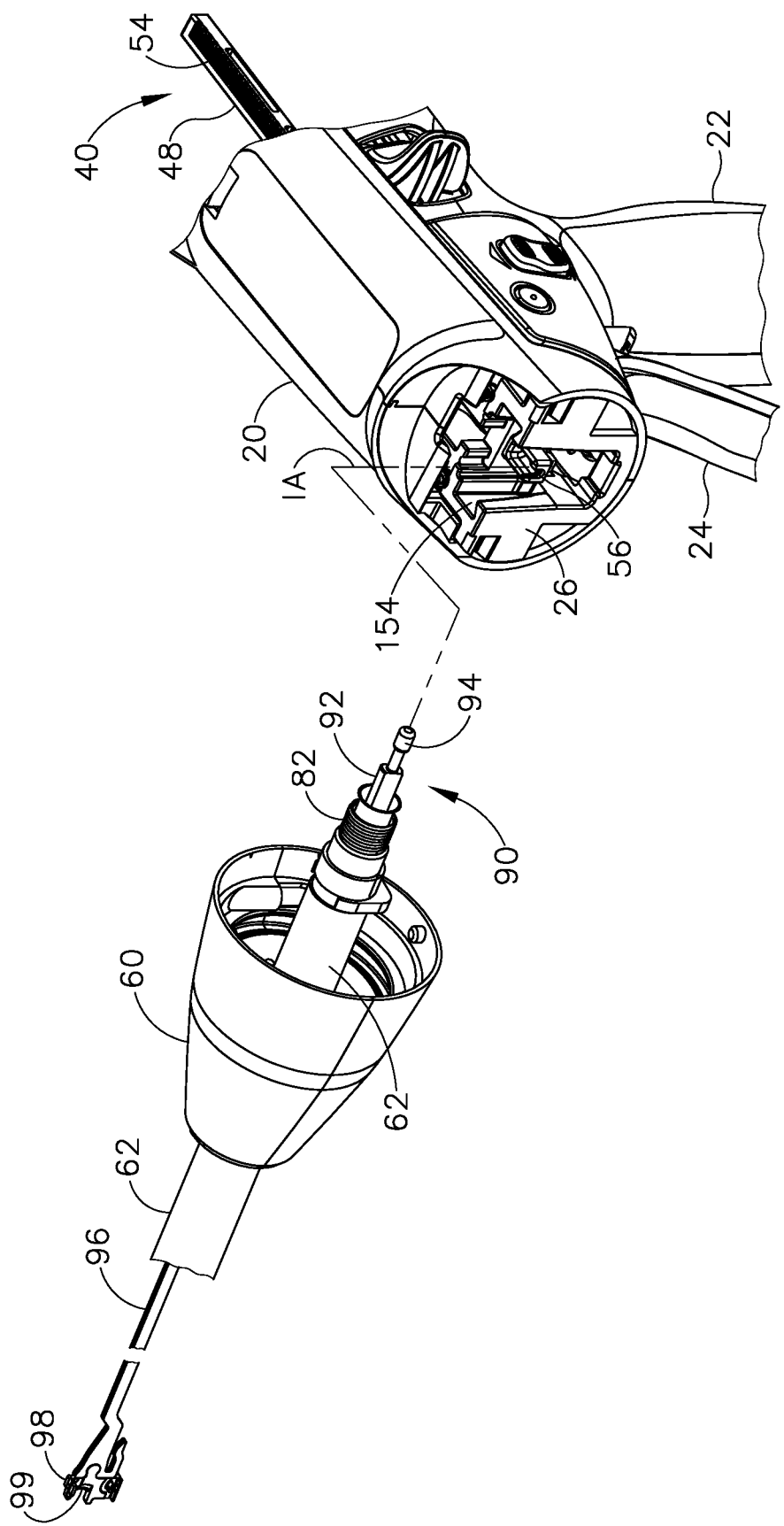
FIG. 5 depicts another perspective view of the surgical instrument of FIG. 1 in a separated state, with certain components of the handle assembly and the shaft assembly omitted to reveal components of a firing system.

As shown best in FIG. 5, elongate drive member (48) of firing drive system (40) includes a rack of teeth (54) formed on at least a proximal portion thereof for meshing engagement with a corresponding drive gear arrangement (not shown) that interfaces with electric motor (42). Drive member (48) further includes an attachment cradle (56) on a distal end thereof, which is configured to receive and couple with an elongate translating member of shaft assembly (14), described below. Drive member (48) is configured to configured to be driven by motor (42) from a proximal position to a distal position to thereby actuate the translating member of shaft assembly (14) and fire end effector (16).

B. Interchangeable Shaft Assembly of Surgical Stapling Instrument

As shown in FIGS. 1-2, interchangeable shaft assembly (14) of the present example includes a proximal nozzle (60), an elongate proximal closure tube (62) extending distally from nozzle (60), an articulation joint (64) disposed at a distal end of the closure tube (62), a distal closure tube segment (66) coupled to a distal end of articulation joint (64), and end effector (16) extending distally therefrom.

End effector (16) includes a first jaw comprising an elongate channel (70) that receives a cartridge (72), and a second jaw comprising an anvil (74) configured to pivot relative to channel (70) between open and closed positions for clamping tissue between anvil (74) and cartridge (72). Cartridge (72) is shown in the form of a conventional staple cartridge having features described in greater detail below, and is configured to fire a plurality of staples into tissue clamped by end effector (16). In other examples, end effector (16) may be suitably configured to apply a variety of other types of motions and energies to tissue captured by end effector (16), such as radio frequency (RF) energy and/or ultrasonic energy, for example. For instance, cartridge (72) may be configured to apply RF to tissue as generally disclosed in U.S. Ser. No. 15/636,096, entitled "Surgical System Couplable With Staple Cartridge And Radio Frequency Cartridge, And Method Of Using Same," filed Jun. 28, 2017, published as U.S. Pub. No. 2019/0000478 on Jan. 3, 2019, the disclosure of which is incorporated by reference herein.

Anvil (74) of end effector (16) is operatively coupled with closure drive system (30) of handle assembly (12), and is configured to pivot between open and closed positions, about a pivot axis that extends transversely to shaft axis (SA), in response to actuation of closure trigger (24). In particular, anvil (74) is configured to as assume an open position when closure trigger (24) is in the unactuated position, and a closed position when closure trigger (24) depressed to the actuated position. Anvil (74) is coupled with closure drive system (30) via proximal closure tube (62) and distal closure tube segment (66), among other components described below. Proximal closure tube (62) and distal closure tube segment (66) are configured to translate proximally and distally relative to nozzle (60) to thereby actuate anvil (74) about its pivot axis in response to actuation of closure trigger (24).

Articulation joint (64) is configured to provide articulation of end effector (16) relative to proximal closure tube (62) and corresponding components of shaft assembly (14) about an articulation axis (AA) that extends transversely to shaft axis (SA). In some examples, end effector (16) may be articulated to a desired orientation by pushing end effector (16) against soft tissue and/or bone within the patient. In other examples, end effector (16) may be articulated by an articulation driver (not shown).

As best seen in FIG. 4, nozzle (60) of interchangeable shaft assembly (14) houses a support structure in the form of a tool chassis (80) that rotatably supports nozzle (60). Nozzle (60) and end effector (16) are configured to rotate relative to tool chassis (80) about shaft axis (SA), as indicated in FIG. 1. As shown in FIG. 5, proximal closure tube (62) houses an internal spine (82) that is rotatably supported by tool chassis (80) (omitted from view in FIG. 5) at a proximal end and is coupled to end effector (16) at a distal end. Tool chassis (80) further supports a closure shuttle (84) that is configured to translate proximally and distally relative to tool chassis (80). A distal end of closure shuttle (84) is coupled to and rotatably supports a proximal end of proximal closure tube (62). A proximal end of closure shuttle (84) includes a pair of proximally extending hooks (86) configured to couple with closure drive system (30) of handle assembly (12). In particular, hooks (86) are configured to releasably capture attachment pin (34) of closure drive system (30) when interchangeable shaft assembly (14) is coupled with handle assembly (12). Accordingly, actuation of closure trigger (24) to the actuated position (see FIG. 3B) drives closure shuttle (84) distally, which in turn drives proximal closure tube (62) and distal closure tube segment (66) distally, thereby actuating anvil (74) to a closed position for clamping tissue with end effector (16). Returning trigger to the unactuated position (see FIG. 3A) actuates these components proximally, thereby returning anvil (74) to an open position.

As seen best in FIG. 5, interchangeable shaft assembly (14) further includes an internal firing system (90) configured to operatively couple with firing drive system (40) of handle assembly (12) when shaft assembly (14) is coupled to handle assembly (12). Firing system (90) includes an intermediate firing shaft (92) slidably received within spine (82) and proximal closure tube (62). Intermediate firing shaft (92) includes a proximal end having an attachment lug (94) configured to rotatably seat within attachment cradle (56) of drive member (48) of firing drive system (40), and a distal end configured to couple to an elongate knife bar (96). Knife bar (96) is connected at its distal end to a knife member (98), which includes a sharpened cutting edge (99) configured to sever tissue clamped by end effector (16) as knife member advances distally through staple cartridge (72). Accordingly, actuation of firing trigger (50) actuates drive member (48) distally, which in turn drives intermediate firing shaft (92), knife bar (96), and knife member (98) distally to thereby cut tissue and simultaneously fire staple cartridge (72), as described below. Knife member (98) may include one or more anvil engagement features configured to engage and maintain anvil (74) in a closed state throughout cutting and stapling of tissue.

Figure 6:
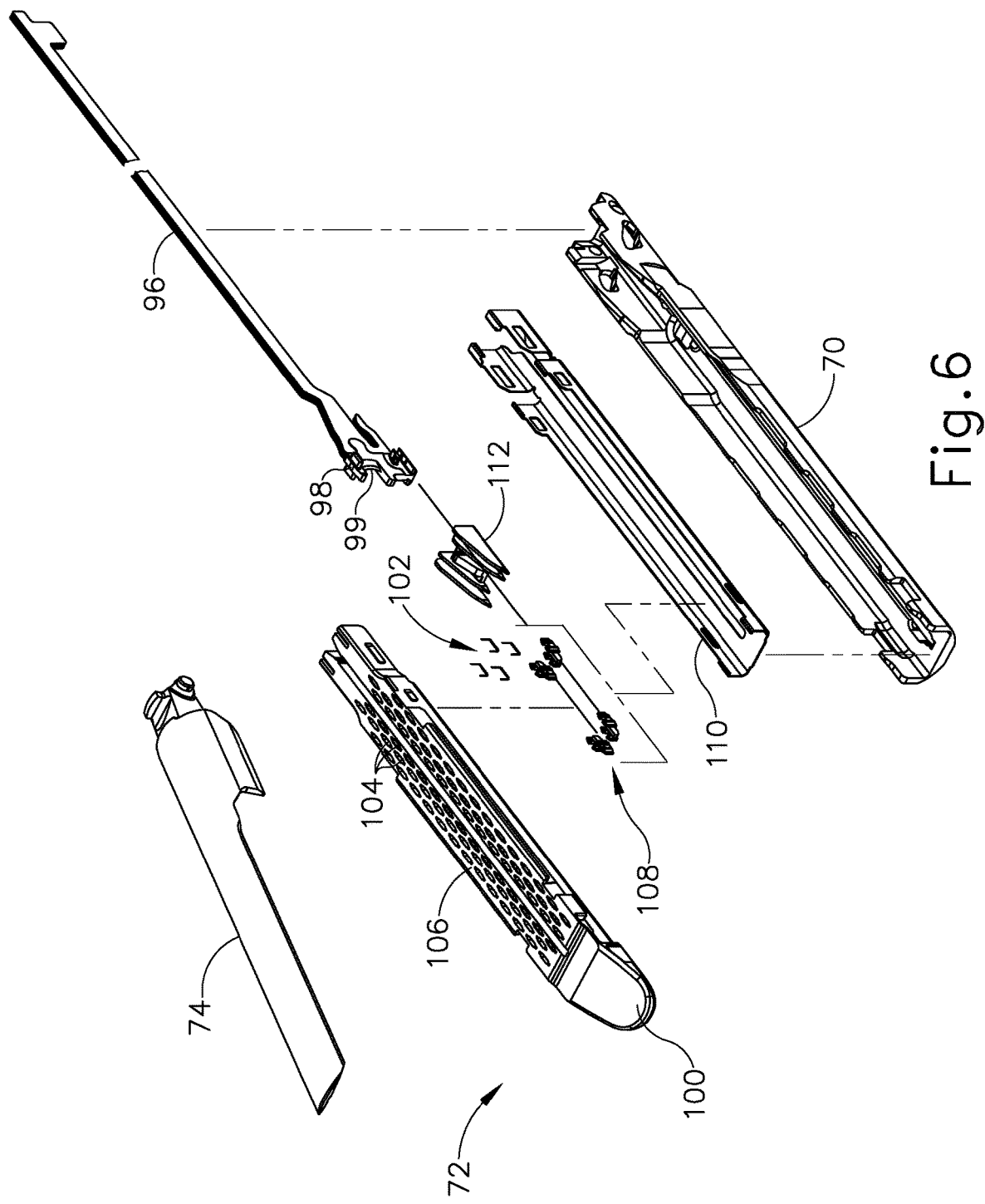
FIG. 6 depicts an exploded perspective view of an end effector of the surgical instrument of FIG. 1, in combination with certain components of the firing system.

As seen best in FIG. 6, staple cartridge (72) includes a molded cartridge body (100) that houses a plurality of staples (102) within staple cavities (104) that open upwardly through a staple deck (106) of cartridge body (100). A plurality of staple drivers (108) are positioned within staple cavities (104), beneath staples (102). A cartridge tray (110) covers an open bottom side of cartridge body (100) and holds together the various components of staple cartridge (72). A wedge sled (112) is slidably received within slots formed in cartridge body (100), and is driven distally by knife member (98) upon actuation of firing drive system (40). As wedge sled (112) advances distally through staple cartridge (72), wedge sled (112) cams staple drivers (108) upwardly to thereby drive staples (102) through tissue clamped by anvil (74) and into staple forming pockets (not shown) formed in anvil (74), thereby deforming staples (102). Simultaneously, cutting edge (99) of knife member (98) severs the tissue clamped in end effector (16). After firing staple cartridge (72), knife member (98) may be retracted to a proximal position to thereby permit opening of anvil (74) and release of the stapled/severed tissue.

C. Electrical Connections Within Surgical Instrument

Interchangeable shaft assembly (14) and variations thereof that are suitable for use with handle assembly (12) may employ one or more sensors and/or various other electrical components that require electrical communication with handle circuit board (46) of handle assembly (12). For instance, a proximal portion of shaft assembly (14) and/or end effector (16) may include one or more sensors (see e.g., FIG. 8) and/or one or more RF electrodes (not shown) configured to electrically couple with handle circuit board (46) to enable operation thereof. As described below, shaft assembly (14) is suitably configured to enable rotation of end effector (16), among other components of shaft assembly (14), relative to handle assembly (12) while maintaining electrical coupling between shaft assembly (14) and handle assembly (12).

Figure 7:
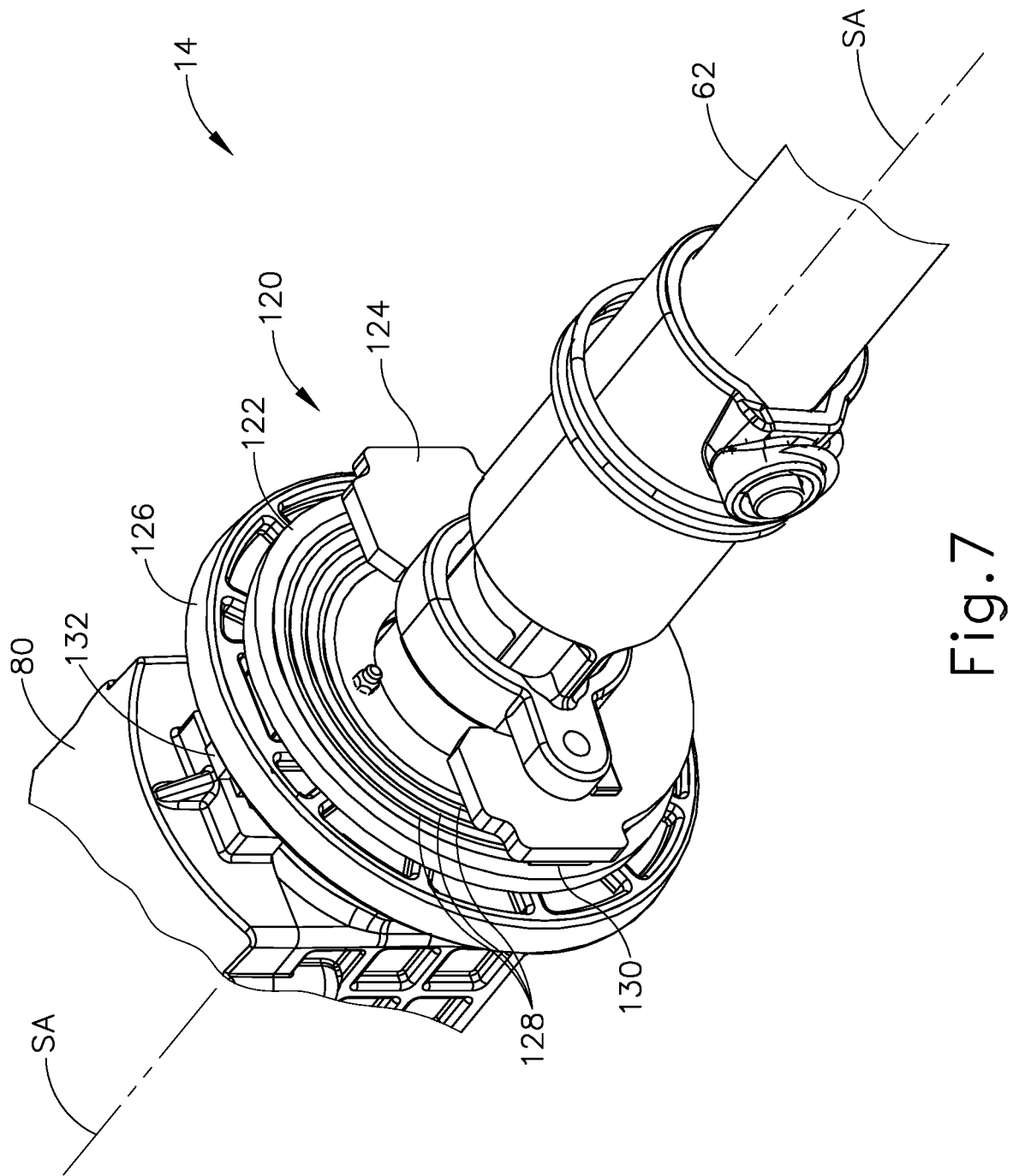
FIG. 7 depicts a perspective view of a proximal portion of the interchangeable shaft assembly of the surgical instrument of FIG. 1, with a nozzle of the shaft assembly omitted to reveal details of an internal slip ring assembly.

As shown in FIG. 7, interchangeable shaft assembly (14) includes a slip ring assembly (120) housed within nozzle (60). Slip ring assembly (120) is configured to electrically couple shaft assembly (14) with handle assembly (12) for communication of electrical power and/or sensor signals between end effector (16) and handle circuit board (46). Slip ring assembly (120) is configured to provide such electrical communication while facilitating rotation of nozzle (60) and end effector (16), among other rotating components of shaft assembly (14), relative to tool chassis (80) and handle assembly (12) about shaft axis (SA). Slip ring assembly (120) comprises a proximal connector flange (122) mounted to a chassis flange (126) that extends distally from tool chassis (80), and a distal connector flange (124) secured to an interior of nozzle (60). Distal connector flange (124) is configured to rotate with nozzle (60) relative to tool chassis (80) and chassis flange (126). Accordingly, the proximal face of distal connector flange (124) confronts and is configured to rotate relative to a distal face of proximal connector flange (122), about shaft axis (SA).

The distal face of proximal connector flange (122) of slip ring assembly (120) includes a plurality of annular conductors (128) arranged substantially concentrically. The proximal face of distal connector flange (124) supports one or more electrical coupling members (130) each supporting a plurality of electrical contacts (not shown). Each electrical contact is positioned to contact a respective annular conductor (128) of proximal connector flange (122). Such an arrangement permits relative rotation between proximal connector flange (122) and distal connector flange (124) while maintaining electrical contact therebetween. Proximal connector flange (122) includes an electrical connector (132) extending proximally from a proximal face of proximal connector flange (122). Electrical connector (132) is configured to electrically couple annular conductors (128) with a shaft circuit board (134), shown schematically in FIG. 4, which may be mounted to shaft chassis (80) and include a microcontroller.

D. Attachment of Interchangeable Shaft Assembly to Handle Assembly

As described in greater detail below, interchangeable shaft assembly (14) is configured to be releasably coupled with handle assembly (12). It will be appreciated that various other types of interchangeable shaft assemblies having end effectors configured for various types of surgical procedures may be used in combination with handle assembly (12) described above.

As shown best in FIG. 4, a proximal end of tool chassis (80) of interchangeable shaft assembly (14) includes a pair of tapered attachment members (150) extending transversely to shaft axis (SA), and a shaft-side electrical connector (152) positioned therebetween. Shaft electrical connector (152) is in electrical communication with shaft circuit board (134) of shaft assembly (14). A distal end of handle frame (26) of handle assembly (12) includes a pair of dovetail receiving slots (154), and a handle-side electrical connector (156) arranged therebetween. Handle electrical connector (156) is in electrical communication with handle circuit board (46) of handle assembly (12). During attachment of shaft assembly (14) to handle assembly (12), as described below, tapered attachment members (150) are received within dovetail receiving slots (154) along an installation axis (IA) that is transverse to shaft axis (SA). Additionally, shaft electrical connector (152) is electrically coupled with handle electrical connector (156). The proximal end of interchangeable shaft assembly (14) additionally includes a latch assembly (158) configured to releasably latch tool chassis (80) to handle frame (26) of handle assembly (12) when shaft assembly (14) is coupled with handle assembly (12).

As shown in FIG. 4, to attach interchangeable shaft assembly (14) to handle assembly (12), the clinician first aligns tapered attachment members (150) of tool chassis (80) with dovetail receiving slots (154) of handle frame (26). The clinician then moves shaft assembly (14) toward handle assembly (12) along installation axis (IA), thereby seating tapered attachment members (150) within dovetail receiving slots (154) and lockingly engaging latch assembly (158) with a distal portion of handle assembly (12). In doing so, attachment lug (94) of intermediate firing shaft (92) is also seated within cradle (56) of longitudinally movable drive member (48), thereby operatively coupling firing system (90) of shaft assembly (14) with firing drive system (40) of handle assembly (12). Additionally, proximal hooks (86) of closure shuttle (84) slide over and capture opposed lateral ends of attachment pin (34) extending from closure link (32), thereby operatively coupling the anvil closure components of shaft assembly (14) with closure drive system (30) of handle assembly (12). Additionally, during attachment of shaft assembly (14) with handle assembly (12), shaft electrical connector (152) on tool chassis (80) is electrically coupled with handle electrical connector (156) on handle frame (26), thereby placing shaft circuit board (134) of shaft assembly (14) in electrical communication with handle circuit board (46) of handle assembly (12).

In various examples, surgical instrument (10) may be further configured in accordance with one or more teachings of U.S. Pat. No. 9,345,481, entitled "Staple Cartridge Tissue Thickness Sensor System," issued May 24, 2016; U.S. Pat. No. 8,608,045, entitled "Powered Surgical Cutting and Stapling Apparatus With Manually Retractable Firing System," issued Dec. 17, 2013; U.S. Ser. No. 15/635,663, entitled "Method For Articulating A Surgical Instrument," filed Jun. 28, 2017, published as U.S. Pub. No. 2019/0000465 on Jan. 3, 2019; U.S. Ser. No. 15/635,631, entitled "Surgical Instrument With Axially Moveable Closure Member," filed Jun. 28, 2017, issued as U.S. Pat. No. 10,639,037 on May 5, 2020; U.S. Ser. No. 15/635,837, entitled "Surgical Instrument Comprising An Articulation System Lockable To A Frame," filed Jun. 28, 2017, published as U.S. Pub. No. 2019/0000472 on Jan. 3, 2019; U.S. Pat. Pub. No. 2016/0066911, entitled "Smart Cartridge Wake Up Operation And Data Retention," published Mar. 10, 2016, issued as U.S. Pat. No. 10,135,242 on Nov. 20, 2018; U.S. Pat. Pub. No. 2015/0272575, entitled "Surgical Instrument Comprising A Sensor System," published Oct. 1, 2015, issued as U.S. Pat. No. 9,913,642 on Mar. 13, 2018; U.S. Pat. Pub. No. 2014/0263552, entitled "Staple Cartridge Tissue Thickness Sensor System," published Sep. 18, 2014, now abandoned; and/or U.S. Pat. Pub. No. 2014/0263541, entitled "Articulatable Surgical Instrument Comprising An Articulation Lock," published Sep. 18, 2014, now abandoned, the disclosures of which are incorporated by reference herein.

E. Exemplary End Effector with Sensors

In some instances, it may be desirable to provide the end effector of a surgical instrument with one or more sensors for sensing various operating conditions of the end effector. Such sensed conditions can then be communicated as electrical signals to a controller of the surgical instrument, such as a controller of shaft circuit board (134) and/or handle circuit board (46) of instrument (10) described above. The controller(s) may then take one or more actions in response to receiving such signals, such as providing one or more indications to the clinician operating the instrument.

Figure 8:
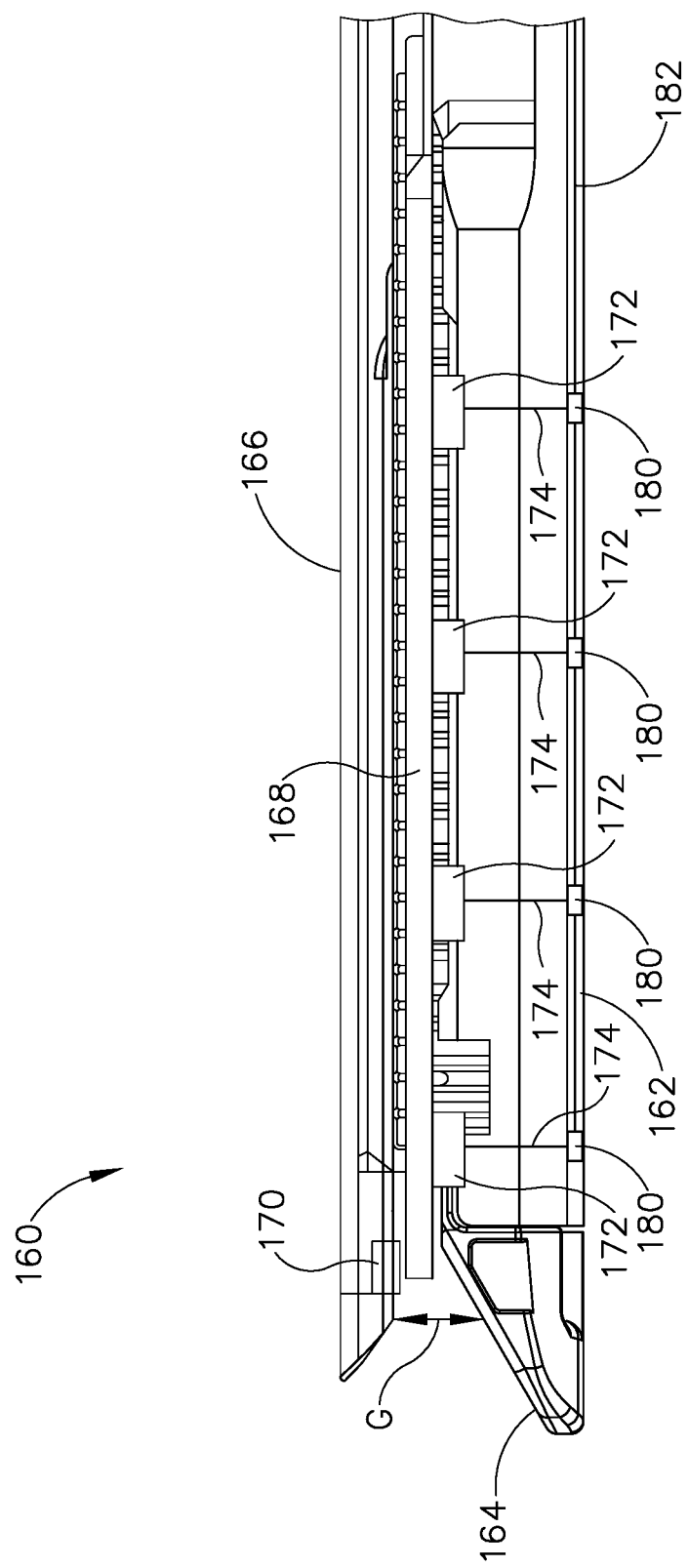
FIG. 8 depicts a side elevational view of another exemplary end effector having a plurality of sensors.

FIG. 8 illustrates an exemplary alternative end effector (160) suitable for use with surgical instrument (10) described above. End effector (160) is similar to end effector (16) described above in that end effector (160) includes a first jaw comprising an elongate channel (162) that receives a staple cartridge (164), and a second jaw comprising an anvil (166) configured to pivot relative to channel (162) between open and closed positions for clamping tissue (168) between anvil (166) and staple cartridge (164). Staple cartridge (164) may be similar to staple cartridge (72) described above.

End effector (160) differs from end effector (16) in that end effector (160) includes a first sensor (170) disposed on a tissue clamping side of anvil (166), and a plurality of second sensors (172) spaced along a length of channel (162). In other versions, one or more sensors, such as one or more of second sensors (172), may be provided on staple cartridge (164). In the present example, first sensor (170) is configured to detect one or more conditions of end effector (160), such as a gap (G) between anvil (166) and staple cartridge (164), which may correspond to a thickness of tissue (168) clamped by end effector (160). Second sensors (172) are also configured to detect one or more conditions of end effector (160) and/or of tissue (168) clamped by end effector (160). For instance, second sensors (172) may be configured to detect one or more conditions such as a color of staple cartridge (164), a length of staple cartridge (164), a clamping condition of end effector (160), and/or the number of actual and/or remaining uses of end effector (160) and/or staple cartridge (164), for example. While end effector (160) is shown having one first sensor (160) and four second sensors (172), various other suitable quantities and arrangements of sensors (170, 172) may be provided in other examples.

Each sensor (170, 172) may comprise any sensor type suitable for measuring the respective one or more conditions of end effector (160). For instance, each sensor (170, 172) may comprise a magnetic sensor (e.g., a Hall effect sensor), a strain gauge, a pressure sensor, an inductive sensor (e.g., an eddy current sensor), a resistive sensor, a capacitive sensor, or an optical sensor, for example. Each sensor (170, 172) is configured to communicate electrical signals corresponding to a sensed condition of end effector (160) to shaft circuit board (134), which may in turn communicate information based on the signals to handle circuit board (46), via slip ring assembly (120) described above.

It should be understood that channel (162) may selectively receive staple cartridge (164) such that staple cartridge (164) may be attached to channel (162), used in accordance with the description herein, removed from channel (162), and replaced with an unused, second staple cartridge (164). Therefore, in versions in which second sensors (172) are provided on staple cartridge (164), second sensors (172) may be configured to selectively establish an electrical connection with shaft circuit board (134) once staple cartridge (164) is suitably coupled to channel (162). In the current example, second sensors (172) each include an electrical contact (174), while channel (162) includes a plurality of electrical contacts (180). Corresponding contacts (174, 180) are dimensioned to electrically couple with each other when staple cartridge (164) is suitably coupled with channel (162). Additionally, channel (162) includes electrical traces (182) extending from contacts (180) all the way to electrical coupling member (130) of slip ring assembly (120). Therefore, when staple cartridge (164) is suitably coupled with channel (162), second sensors (172) are in electrical communication with shaft circuit board (134).

II. Exemplary Sealable Electrical Connection Assemblies

During use of surgical instrument (10) in surgical procedures, the electrical connection formed between handle assembly (12) and shaft assembly (14), via electrical connectors (152, 156), may be vulnerable to fluid ingress. Such fluid ingress can undesirably cause shorting of the electrical pathways in surgical instrument (10), which could result in failure of one or more electrical systems of instrument (10). The exemplary sealable electrical connection assemblies described below provide a substantially liquid-tight seal that circumferentially surrounds (or otherwise fully surrounds) the electrical connection established between shaft assembly (14) and handle assembly (12) when coupled together. This liquid-tight seal protects the electrical connection from unwanted exposure to liquids that might otherwise cause electrical shorting.

It will be understood that each such sealable electrical connection assembly described below is suitable for use with surgical instrument (10), for instance in place of electrical connectors (152, 156). As described in greater detail below, each sealable electrical connection assembly includes a first connector portion supported by a distally facing portion of handle frame (26) of handle assembly (12), and an opposed second connector portion supported by a proximally facing portion of tool chassis (80) of interchangeable shaft assembly (14). The first connector portion includes a plurality of first electrical contacts and a first sealing portion positioned adjacent to the first electrical contacts. The second connector portion includes a plurality of second electrical contacts and a second sealing portion positioned adjacent to the second electrical contacts. Throughout the exemplary configurations described below, it will be appreciated that the first and second electrical contacts may be of any suitable type known in the art, such as leaf spring contacts or spring-loaded pogo pins, for example.

When shaft assembly (14) is assembled with handle assembly (12) along installation axis (IA) in the manner described above, the first and second electrical contacts mechanically and electrically engage to establish an electrical connection. Simultaneously, the first and second sealing portions sealingly engage one another to establish a liquid-tight seal that circumferentially surrounds the engaged electrical contacts to thereby protect the electrical connection from unwanted exposure to liquids. The electrical and sealing engagement between the first and second connector portions is fully established when shaft assembly (14) fully seats with handle assembly (12), for example when latch assembly (158) of shaft assembly (14) lockingly engages handle assembly (12).

A. Sealable Electrical Connection Assembly Having Wiper and Fluid Drainage Opening FIGS. 9A and 9B show a first exemplary sealable electrical connection assembly (200) suitable for use with surgical instrument (10). Sealable electrical connection assembly (200) includes a first connector (202) that is supported by and is fixed relative to a distally facing portion of handle frame (26) of handle assembly (12). First connector (202) includes a plurality of first electrical contacts (204) and a first sealing portion (206). Connection assembly (200) further includes a second connector (208) that is supported by and is fixed relative to a proximally facing portion of tool chassis (80) of shaft assembly (14). Second connector (208) includes a plurality of second electrical contacts (210) and a second sealing portion (212). First electrical contacts (204)

are in electrical communication with handle circuit board (46), and second electrical contacts (210) are in electrical communication with shaft circuit board (134). In other examples, a reverse configuration may be provided in which first connector (202) is coupled to shaft assembly (14) and second connector (208) is coupled to handle assembly (12).

First sealing portion (206) of first connector (202) includes a first side sealing element (214) that extends vertically along a first side of first electrical contacts (204), and which has a first lower leg (216) that extends laterally inwardly across a first portion of the lower side of second electrical contacts (210). First sealing portion (206) further includes a second side sealing element (218) that extends vertically along an opposed second side of first electrical contacts (204), and which has a second lower leg (220) that extends laterally inwardly across a second portion of the lower side of second electrical contacts (210), toward first lower leg (216). Accordingly, first and second side sealing elements (214, 218) of the present example are each formed with an L-like shape. The confronting lower ends of side sealing elements (214, 218), defined by lower legs (216, 220), define an opening (222) therebetween.

Second sealing portion (212) of second connector (208) includes an upper sealing element (224) that spans laterally across an upper side of second electrical contacts (210), and a lower sealing element (226) that spans laterally across an opposed lower side of second electrical contacts (210). In the present example, upper and lower sealing elements (224, 226) are each formed with a linear shape, and are substantially centered relative to second electrical contacts (210). Additionally, upper sealing element (224) is formed with a greater lateral width than lower sealing element (226). In particular, as shown in FIG. 9B, upper sealing element (224) is sized to span across and sealingly engage the upper free ends of side sealing elements (214, 218) of first sealing portion (206). Additionally, lower sealing element (226) is sized to span between and sealingly engage the inner surfaces of side sealing elements (214, 218), and the upper surfaces of lower legs (216, 220). Sealing elements (214, 218, 224, 226) may be formed of a flexible elastomeric material, such as santoprene for example.

FIG. 9A shows second connector (208) positioned vertically above first connector (202) as the proximal end of shaft assembly (14) is aligned with the distal end of handle assembly (12) along installation axis (IA). As shaft assembly (14) slides downwardly along installation axis (IA) into engagement with handle assembly (12) in the manner described above, lower sealing element (226) of second sealing portion (212) is directed downwardly between side sealing elements (214, 218) of first sealing portion (206). Lower sealing element (226) contacts and drags downwardly over first electrical contacts (204), thereby wiping any liquid from first contacts (204) and driving the liquid downwardly through opening (222), which drains the wiped liquid away from electrical connection contacts (204, 210) and toward an exterior of surgical instrument (10).

As the proximal end of shaft assembly (14) fully seats with the distal end of handle assembly (12), second connector (208) fully seats with first connector (202) as shown in FIG. 9B. As second connector (208) reaches a fully seated position, first and second electrical contacts (204, 210) electrically couple to establish an electrical connection between handle assembly (12) and shaft assembly (14). Simultaneously, lower sealing element (226) of second sealing portion (212) closes lower opening (222) of first sealing portion (206), and sealing portions (206, 212) sealingly engage one another as well as an opposing surface of handle assembly (12) or shaft assembly (14). For example, the distal faces of side sealing elements (214, 218) may sealingly engage one or more proximal surfaces of tool chassis (80) or other proximal surfaces supported by tool chassis (80). Additionally, the proximal faces of upper and lower sealing elements (224, 226) may sealingly engage one or more distal surfaces of handle frame (26) or other distal surfaces supported by handle frame (26). In this manner, first and second sealing portions (206, 212) establish a liquid-tight seal that circumferentially surrounds the electrical connection and protects it from unwanted exposure to liquids that might otherwise cause electrical shorting.

Accordingly, first and second sealing portions (206, 212) combine to define a sealing layer between shaft assembly (14) and handle assembly (12). In the present example, first and second sealing portions (206, 212) combine to define a seal plane that extends transversely to the longitudinal axis of shaft assembly (14), and generally parallel to installation axis (IA). It will be understood that sealable electrical connection assemblies (230, 260, 270, 300, 330, 360, 400) described below each define a seal plane of a similar orientation.

B. Sealable Electrical Connection Assembly Having Inverted U-Shaped Sealing Element and Wiper FIGS. 10A and 10B show another exemplary sealable electrical connection assembly (230) suitable for use with surgical instrument (10). Sealable electrical connection assembly (230) includes a first connector (232) that is supported by and is fixed relative to a distally facing portion of handle frame (26) of handle assembly (12). First connector (232) has a plurality of first electrical contacts (234) and a first sealing portion (236). Connection assembly (230) further includes a second connector (238) that is supported by and is fixed relative to a proximally facing portion of tool chassis (80) of shaft assembly (14). Second connector (238) has a plurality of second electrical contacts (240) and a second sealing portion (242). First electrical contacts (234) are in electrical communication with handle circuit board (46), and second electrical contacts (240) are in electrical communication with shaft circuit board (134). In other examples, a reverse configuration may be provided in which first connector (232) is coupled to shaft assembly (14) and second connector (238) is coupled to handle assembly (12).

First sealing portion (236) of first connector (232) is in the form of an inverted U-shaped sealing element having a first side portion (244) that extends vertically along a first side of first electrical contacts (234), an opposed second side portion (246) that extends vertically along an opposed second side of first electrical contacts (234), and an upper portion (248) that extends laterally across an upper side of first electrical contacts (234). Free lower ends of first and second side portions (244, 246) define a lower opening (250) therebetween that is configured to drain fluid in a manner similar to lower opening (222) of first sealing portion (206) described above. Second sealing portion (242) of second connector (238) is similar to lower sealing element (226) described above in that second sealing portion (242) is in the form of a linear sealing element sized to span between and sealingly engage the inner surfaces of side portions (244, 246) of first sealing portion (236). Sealing portions (236, 242) may each be formed of a flexible elastomeric material, such as santoprene for example.

FIG. 10A shows second connector (238) positioned vertically above first connector (232) as the proximal end of shaft assembly (14) is aligned with the distal end of handle assembly (12) along installation axis (IA). As shaft assembly (14) slides downwardly along installation axis (IA) into engagement with handle assembly (12), second sealing portion (242) contacts and drags downwardly over first electrical contacts (234), thereby wiping any liquid from first contacts (234) and driving the liquid downwardly through opening (250), which drains the wiped liquid away from electrical contacts (234, 240).

Second connector (238) fully seats with first connector (232), as shown in FIG. 10B, when the proximal end of shaft assembly (14) fully seats with the distal end of handle assembly (12). As second connector (238) reaches this fully seated position, first and second electrical contacts (234, 240) electrically couple to establish an electrical connection between handle assembly (12) and shaft assembly (14). Simultaneously, second sealing portion (242) closes lower opening (250) of first sealing portion (236), and sealing portions (236, 242) sealingly engage one another as well as an opposing surface of handle assembly (12) or shaft assembly (14). In this manner, first and second sealing portions (236, 242) establish a liquid-tight seal that circumferentially surrounds the electrical connection and protects it from unwanted exposure to liquids that might otherwise cause electrical shorting.

C. Sealable Electrical Connection Assembly Having Waterproof Mesh

FIGS. 11A and 11B show another exemplary sealable electrical connection assembly (260) suitable for use with surgical instrument (10). Sealable electrical connection assembly (260) is substantially similar to sealable electrical connection assembly (230) described above, as indicated by use of like reference numerals, except as otherwise described below.

Similar to sealable electrical connector (230), sealable electrical connection assembly (260) includes a first connector (262) and a second connector (264) configured to electrically and sealingly couple together when shaft assembly (14) attaches to handle assembly (12). Sealable electrical connection assembly (260) differs in that first connector (262) includes a first layer (266) of liquid-impermeable material, such as waterproof mesh, that lines the inwardly facing surfaces of side portions (244, 246) and upper portion (248) of first sealing portion (236). Additionally, second connector (264) includes a second layer (268) of liquid-impermeable material, such as waterproof mesh, that lines an upper surface thereof. First and second layers (266, 268) may be affixed to first and second connectors (262, 264), respectively, using various suitable means readily apparent to those of ordinary skill in the art. For instance, layers (266, 268) may be secured using threaded fasteners, tack welds, or adhesive. As shown in FIG. 11B, first and second layers (266, 268) are configured to combine to circumferentially surround the electrical connection formed by electrical contacts (234, 240) and thereby enhance the liquid-tight seal established by first and second sealing portions (236, 242) when shaft assembly (14) is attached to handle assembly (12).

D. Sealable Electrical Connection Assembly Having Upright U-Shaped Sealing Element and Wiper FIGS. 12A and 12B show another exemplary sealable electrical connection assembly (270) suitable for use with surgical instrument (10). Sealable electrical connection assembly (270) includes a first connector (272) that is supported by and is fixed relative to a distally facing portion of handle frame (26) of handle assembly (12). First connector (272) has a plurality of first electrical contacts (274) and a first sealing portion (276). Connection assembly (270) further includes a second connector (278) that is supported by and is fixed relative to a proximally facing portion of tool chassis (80) of shaft assembly (14). Second connector (278) has a plurality of second electrical contacts (280) and a second sealing portion (282). First electrical contacts (274) are in electrical communication with handle circuit board (46), and second electrical contacts (240) are in electrical communication with shaft circuit board (134). In other examples, a reverse configuration may be provided in which first connector (272) is coupled to shaft assembly (14) and second connector (278) is coupled to handle assembly (12).

First sealing portion (276) of first connector (272) is in the form of an upright U-shaped sealing element having a first side portion (284) that extends vertically along a first side of first electrical contacts (274), an opposed second side portion (286) that extends vertically along an opposed second side of first electrical contacts (274), and a lower portion (288) that extends laterally across lower side of first electrical contacts (274). Free upper ends of first and second side portions (284, 286) define an upper opening (290) therebetween. Second sealing portion (282) of second connector (278) is in the form of a linear sealing element sized to span between and sealingly engage the inner surfaces of the free upper ends of side portions (284, 286) of first sealing portion (276) when shaft assembly (14) is attached to handle assembly (12). Sealing portions (276, 282) may each be formed of a flexible elastomeric material, such as santoprene for example.

FIG. 12A shows second connector (278) positioned vertically above first connector (272) as the proximal end of shaft assembly (14) is aligned with the distal end of handle assembly (12) along installation axis (IA). As shaft assembly (14) slides downwardly along installation axis (IA) into engagement with handle assembly (12), second sealing portion (272) may contact and drag downwardly over at least a portion of the distal end of handle assembly (12) positioned above first electrical contacts (274), thereby wiping liquid from handle assembly (12).

Second connector (278) fully seats with first connector (272), as shown in FIG. 12B, when the proximal end of shaft assembly (14) fully seats with the distal end of handle assembly (12). As second connector (278) reaches this fully seated position, first and second electrical contacts (274, 280) electrically couple to establish an electrical connection between handle assembly (12) and shaft assembly (14). Simultaneously, second sealing portion (282) closes upper opening (290) of first sealing portion (276), and sealing portions (276, 282) sealingly engage one another as well as an opposing surface of handle assembly (12) or shaft assembly (14). In this manner, first and second sealing portions (276, 282) establish a liquid-tight seal that circumferentially surrounds the electrical connection and protects it from unwanted exposure to liquids that might otherwise cause electrical shorting.

Figure 13:
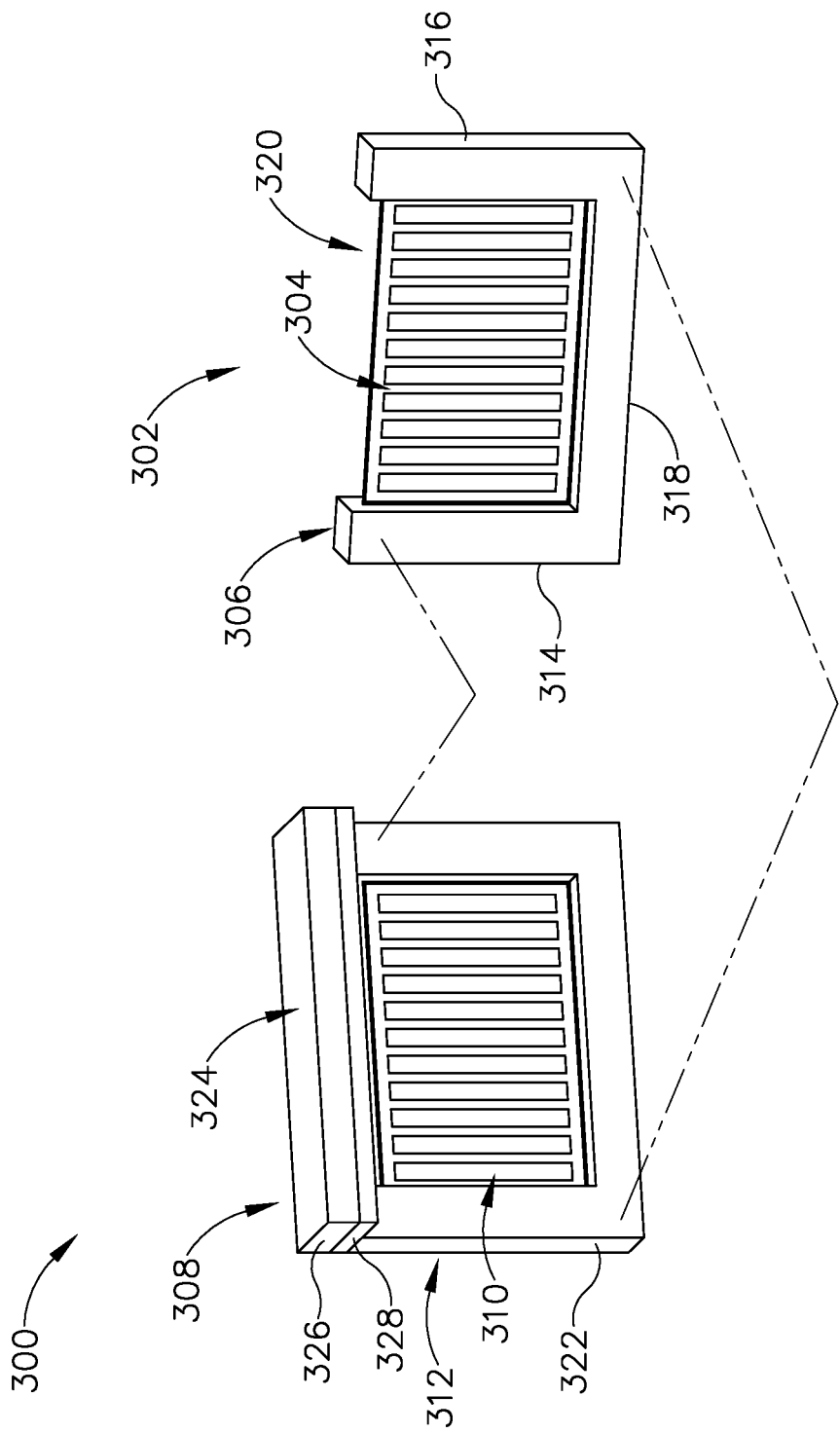
FIG. 13 depicts a schematic perspective view of another exemplary sealable electrical connection assembly suitable for use with the surgical instrument of FIG. 1, showing the first and second portions of the assembly in a disengaged state.

E. Sealable Electrical Connection Assembly Having Sealing Element With Rigid Upper Plate FIG. 13 shows another exemplary sealable electrical connection assembly (300) suitable for use with surgical instrument (10). Sealable electrical connection assembly (300) includes a first connector (302) that is supported by and is fixed relative to a distally facing portion of handle frame (26) of handle assembly (12). First connector (302) has a plurality of first electrical contacts (304) and a first sealing portion (306). Connection assembly (300) further includes a second connector (308) that is supported by and is fixed relative to a proximally facing portion of tool chassis (80) of shaft assembly (14). Second connector (308) has a plurality of second electrical contacts (310) and a second sealing portion (312). First electrical contacts (304) are in electrical communication with handle circuit board (46), and second electrical contacts (310) are in electrical communication with shaft circuit board (134). In other examples, a reverse configuration may be provided in which first connector (302) is coupled to shaft assembly (14) and second connector (308) is coupled to handle assembly (12).

First sealing portion (306) of first connector (302) is in the form of an upright U-shaped sealing element similar to first sealing portion (276) described above. In that regard, first sealing portion (306) has a first side portion (314) that extends vertically along a first side of first electrical contacts (304), an opposed second side portion (316) that extends vertically along an opposed second side of first electrical contacts (304), and a lower portion (318) that extends laterally across lower side of first electrical contacts (304). Free upper ends of first and second side portions (314, 316) define an upper opening (320) therebetween.

Second sealing portion (312) of second connector (308) includes a lower sealing element (322) of a similar upright U-shape, and an upper sealing element (324) that extends laterally and projects proximally beyond an upper end of lower sealing element (322). Upper sealing element (324) includes an upper layer (326) in the form of a rigid plate, and a lower layer (328) in the form of a compressible elastomeric material, such as santoprene for example. Lower sealing element (322) and first sealing portion (306) may be formed of an elastomeric material as well. As described below, lower layer (328) of upper sealing element (324) is configured to sealingly engage the upper free ends of first sealing portion (306) when shaft assembly (14) is attached to handle assembly (12).

Figure 14A:
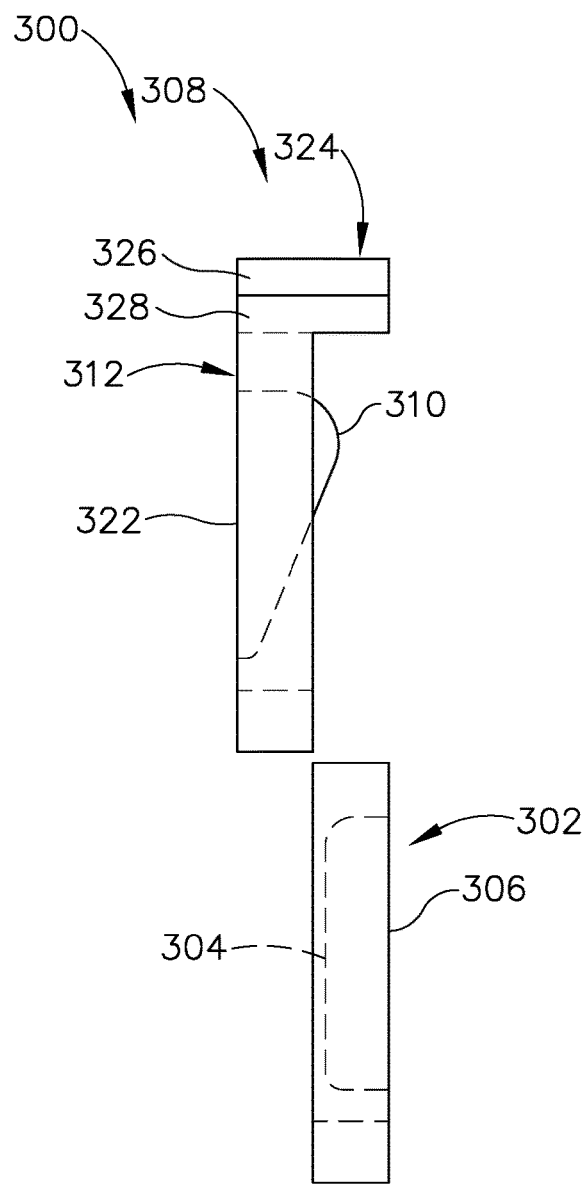
FIG. 14A depicts a schematic side elevational view of the sealable electrical connection assembly of FIG. 13, showing the first and second portions in a disengaged state.
Figure 14B:
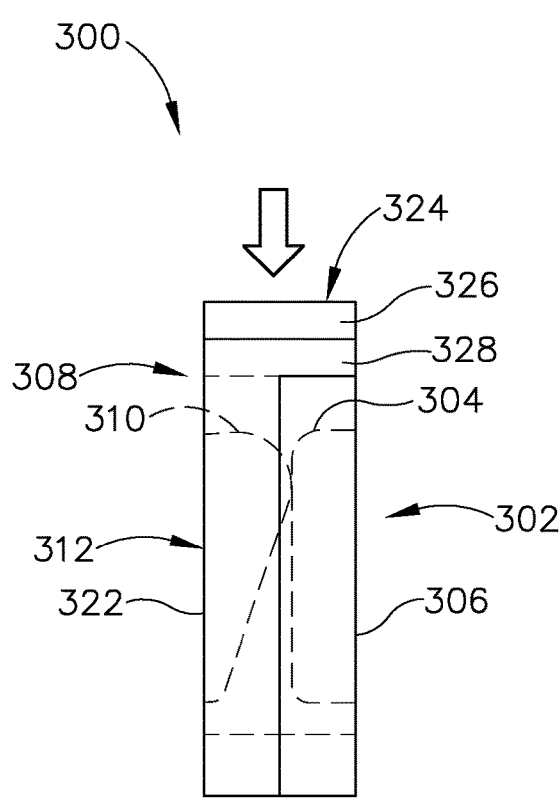
FIG. 14B depicts a schematic side elevational view of the sealable electrical connection assembly of FIG. 14A, showing the first and second portions in an engaged state.

FIG. 14A shows second connector (308) positioned vertically above first connector (302) as the proximal end of shaft assembly (14) is aligned with the distal end of handle assembly (12) along installation axis (IA). As shaft assembly (14) slides downwardly along installation axis (IA) into engagement with handle assembly (12), lower sealing element (322) of second sealing portion (312) confronts first sealing portion (306), and second electrical contacts (310) confront first electrical contacts (304). Second connector (308) fully seats with first connector (302), as shown in FIG. 14B, when the proximal end of shaft assembly (14) fully seats with the distal end of handle assembly (12). As second connector (308) reaches this fully seated position, first and second electrical contacts (304, 310) electrically couple to establish an electrical connection between handle assembly (12) and shaft assembly (14). Simultaneously, the proximal face of lower sealing element (322) of second sealing portion (312) sealingly engages the distal face of first sealing portion (306), and lower layer (328) of upper sealing element (324) sealingly engages the free upper ends of first sealing portion (306), thereby closing upper opening (320). The rigidity of upper layer (326) provides a secure and stable sealing engagement between upper sealing element (324) and first sealing portion (306). In this manner, first and second sealing portions (306, 312) cooperate to establish a liquid-tight seal that circumferentially surrounds the electrical connection and protects it from unwanted exposure to liquids that might otherwise cause electrical shorting.

In some versions of sealable electrical connection assembly (300), the lower portion of lower sealing element (322) may be configured to function as a wiper in a manner similar to sealing element (212, 242) described above. For instance, as shaft assembly (14) slides downwardly along installation axis (IA) into engagement with handle assembly (12), the lower portion of lower sealing element (322) may be received through upper opening (320) of first sealing portion (306), and contact and drag downwardly over first electrical contacts (304) to thereby wipe liquid from first contacts (304).

In other versions of sealable electrical connection assembly (300), lower sealing element (322) may be omitted from second sealing portion (312), leaving only upper sealing element (324). In such versions, first sealing portion (306) may be suitably dimensioned such that the distal face of first sealing portion (306) is configured to sealingly engage a proximal surface of shaft assembly (14), such as a proximal surface of tool chassis (80). Accordingly, first and second sealing portions (306, 312) remain configured to establish a liquid-tight seal that circumferentially surrounds the electrical connection when shaft assembly (14) is attached to handle assembly (12).

Figure 15:
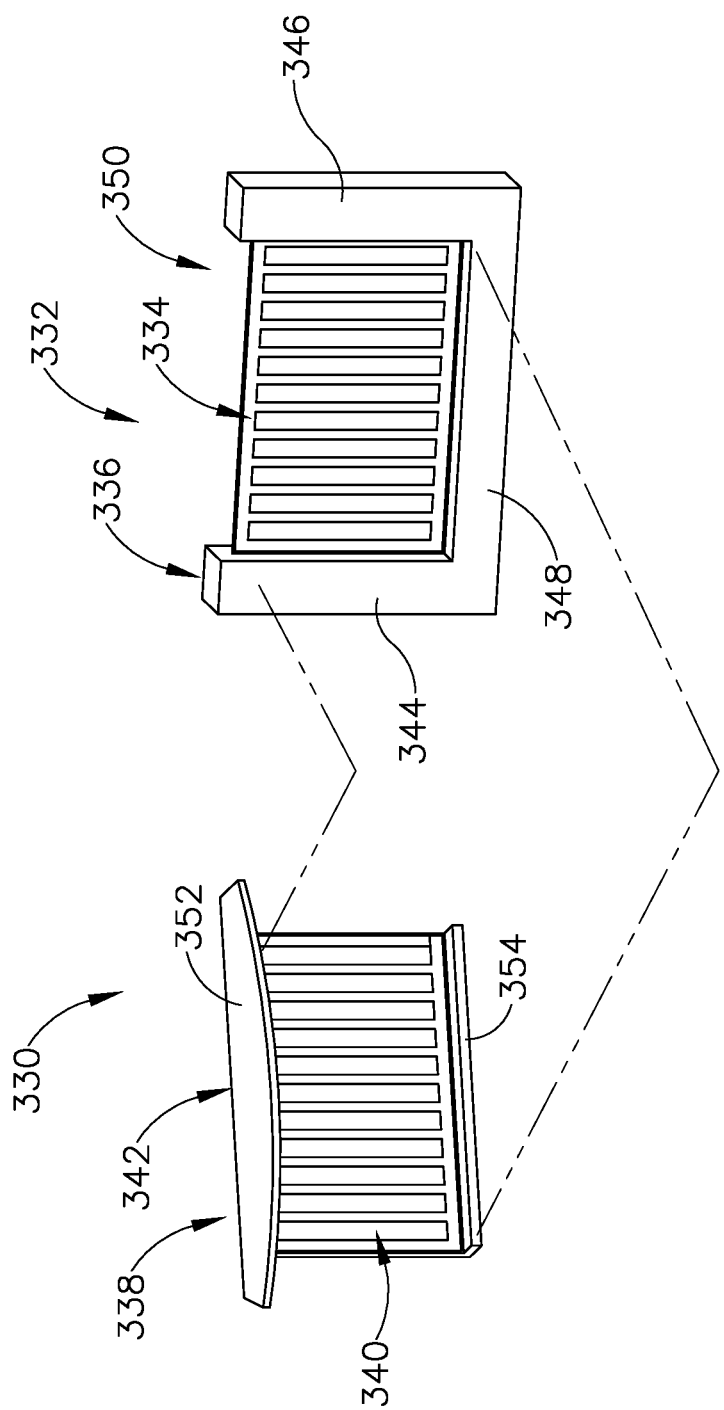
FIG. 15 depicts a schematic perspective view of another exemplary sealable electrical connection assembly suitable for use with the surgical instrument of FIG. 1, showing the first and second portions of the assembly in a disengaged state.

F. Sealable Electrical Connection Assembly Having First Sealing Portion with U-Shaped Sealing Element and Second Sealing Portion with Upper and Lower Sealing Elements FIG. 15 shows another exemplary sealable electrical connection assembly (330) suitable for use with surgical instrument (10). Sealable electrical connection assembly (330) includes a first connector (332) that is supported by and is fixed relative to a distally facing portion of handle frame (26) of handle assembly (12). First connector (332) has a plurality of first electrical contacts (334) and a first sealing portion (336). Connection assembly (330) further includes a second connector (338) that is supported by and is fixed relative to a proximally facing portion of tool chassis (80) of shaft assembly (14). Second connector (338) has a plurality of second electrical contacts (340) and a second sealing portion (312). First electrical contacts (334) are in electrical communication with handle circuit board (46), and second electrical contacts (340) are in electrical communication with shaft circuit board (134). In other examples, a reverse configuration may be provided in which first connector (332) is coupled to shaft assembly (14) and second connector (338) is coupled to handle assembly (12).

First sealing portion (336) of first connector (332) is in the form of an upright U-shaped sealing element similar to first sealing portion (276) described above. In that regard, first sealing portion (336) has a first side portion (344) that extends vertically along a first side of first electrical contacts (334), an opposed second side portion (346) that extends vertically along an opposed second side of first electrical contacts (334), and a lower portion (348) that extends laterally across lower side of first electrical contacts (334). Free upper ends of first and second side portions (344, 346) define an upper opening (350) therebetween.

Second sealing portion (312) of second connector (338) includes an upper sealing element (352) that extends laterally across an upper side of second electrical contacts (340), and a lower sealing element (354) that extends laterally across a lower side of second electrical contacts (340). Upper sealing element (352) projects proximally beyond second electrical contacts (340), and is configured to function in a manner similar to upper sealing element (324) described above, by sealingly engaging upper free ends of first sealing portion (336) when shaft assembly (14) is attached to handle assembly (12), as described below. As shown in the present example, upper sealing element (352) may include a rounded proximal face. First and second sealing portions (336, 342) may each be formed of a flexible elastomeric material, such as santoprene for example.

First and second connectors (332, 338) are configured to engage one another in a manner similar to connectors (272, 278) of connection assembly (300) described above. As shaft assembly (14) slides downwardly along installation axis (IA) into engagement with handle assembly (12), lower sealing element (354) of second sealing portion (312) is received through upper opening (350) of first sealing portion (336). Lower sealing element (354) contacts and drags downwardly over first electrical contacts (334), thereby wiping any liquid from first contacts (334). As second connector (338) fully seats with first connector (332), first and second electrical contacts (334, 340) electrically couple to establish an electrical connection between handle assembly (12) and shaft assembly (14). Simultaneously, upper sealing element (352) sealingly engages the free upper ends of first sealing portion (336), and lower sealing element (354) may sealingly engage lower portion (348) of first sealing portion (336). Additionally, side portions (344, 346) of first sealing portion (336) sealingly engage a proximal surface of shaft assembly (14), such as a proximal surface of tool chassis (80), and the proximal face of upper sealing element (352) sealingly engages a distal surface of handle assembly (12), such as a distal surface of handle frame (26). In this manner, first and second sealing portions (336, 342) cooperate to establish a liquid-tight seal that circumferentially surrounds the electrical connection and protects it from unwanted exposure to liquids that might otherwise cause electrical shorting.

G. Sealable Electrical Connection Assembly Having Accordion Flap

FIG. 16 shows another exemplary sealable electrical connection assembly (360) suitable for use with surgical instrument (10). Sealable electrical connection assembly (360) includes a first connector (362) that is supported by and is fixed relative to a distally facing portion of handle frame (26) of handle assembly (12). First connector (362) has a plurality of first electrical contacts (364) and a first sealing portion (366). Connection assembly (360) further includes a second connector (368) that is supported by and is fixed relative to a proximally facing portion of tool chassis (80) of shaft assembly (14). Second connector (368) has a plurality of second electrical contacts (370) and a second sealing portion (372). First electrical contacts (364) are in electrical communication with handle circuit board (46), and second electrical contacts (370) are in electrical communication with shaft circuit board (134). In other examples, a reverse configuration may be provided in which first connector (362) is coupled to shaft assembly (14) and second connector (368) is coupled to handle assembly (12).

First sealing portion (366) of first connector (362) is in the form of an upright U-shaped sealing element similar to first sealing portion (276) described above. In that regard, first sealing portion (366) has a first side portion (374) that extends vertically along a first side of first electrical contacts (364), an opposed second side portion (376) that extends vertically along an opposed second side of first electrical contacts (364), and a lower portion (378) that extends laterally across lower side of first electrical contacts (364). Free upper ends of first and second side portions (374, 376) define an upper opening (380) therebetween.

Second connector (368) of the present example includes a proximally projecting feature (382) and a pair of side surfaces (384) recessed distally of a proximal face of projecting feature (382). Projecting feature (382) supports second electrical contacts (370) and includes an upper overhang feature (386) that projects proximally beyond second electrical contacts (370) and supports a deformable seal in the form of an accordion flap (388). Accordion flap (388) includes an upper end coupled to overhang feature (386), and an opposed lower end that hangs freely. As described below, accordion flap (388) is configured to transition between an expanded state (FIG. 17A) in which accordion flap (388) covers and protects second electrical contacts (370), and a collapsed state (FIG. 17C) in which flap (388) reveals second contacts (370) to permit coupling of second contacts (370) with first contacts (364). The proximally facing features of second connector (368), including projecting feature (382), side surfaces (384), overhang feature (386), and accordion flap (388), collectively define second sealing portion (372). In the present example, first sealing portion (366) and at least accordion flap (388) of second sealing portion (372) may be formed of a flexible elastomeric material, such as santoprene for instance. In some examples, projecting feature (382) and/or overhang feature (386) may also be formed of a flexible elastomeric material.

Figures 17A, 17B, 17C:
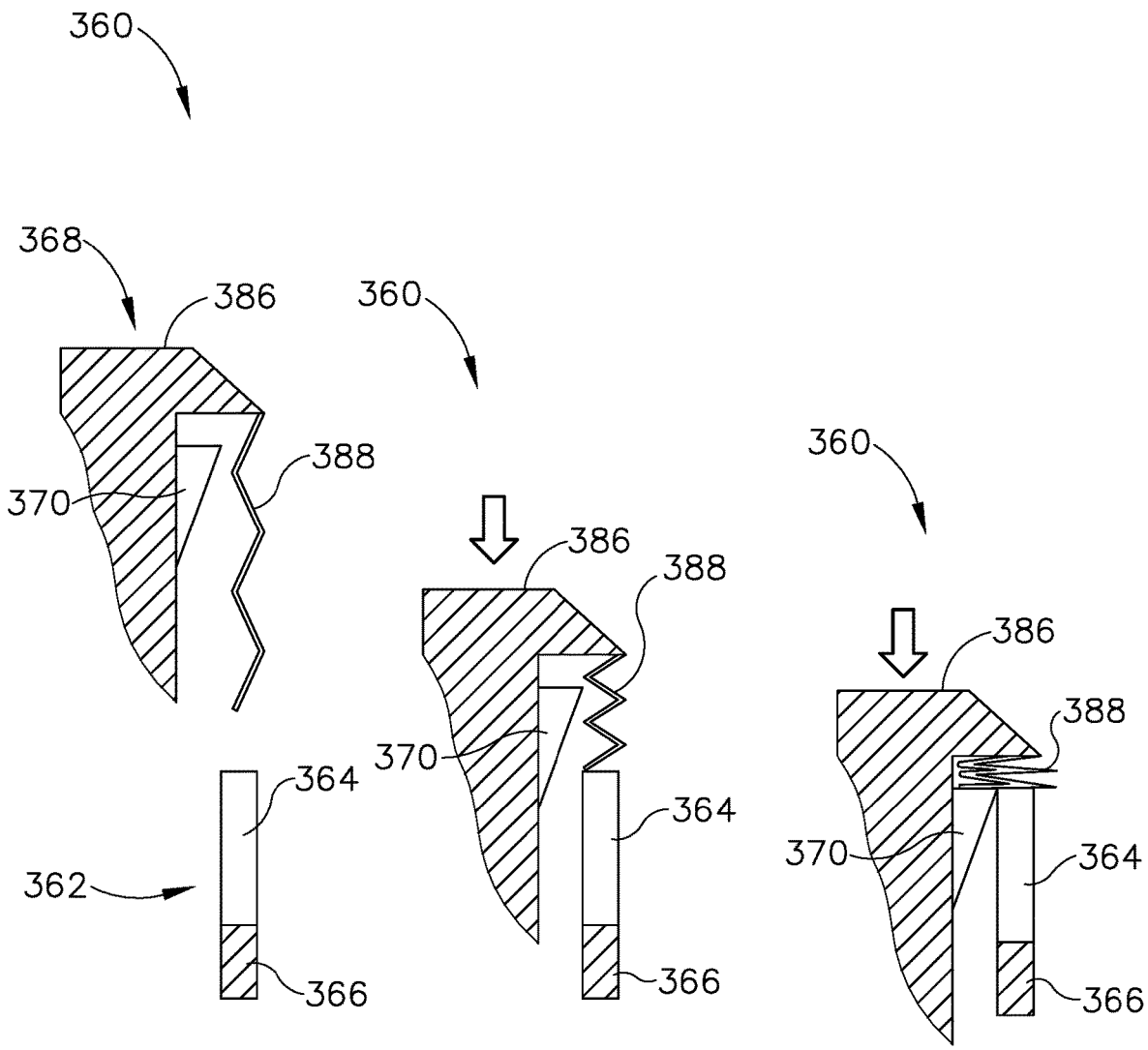
FIG. 17A depicts a side cross-sectional view of the sealing electrical connection assembly of FIG. 16, showing the first and second portions in a disengaged state.
FIG. 17B depicts a side cross-sectional view of the sealing electrical connection assembly of FIG. 17A, showing the first and second portions in a partially engaged state.
FIG. 17C depicts a side cross-sectional view of the sealing electrical connection assembly of FIG. 17B, showing the first and second portions in a fully engaged state.

FIG. 17A shows second connector (368) positioned vertically above first connector (362) as the proximal end of shaft assembly (14) is aligned with the distal end of handle assembly (12) along installation axis (IA). As shaft assembly (14) slides downwardly along installation axis (IA) into engagement with handle assembly (12), the lower end of accordion flap (388) is received through upper opening (380) of first sealing portion (366) and contacts the upper edges of first electrical contacts (364). As shown in FIG. 17B, continued downward advancement of shaft assembly (14) along installation axis (IA) causes first electrical contacts (364) to drive accordion flap (388) upwardly toward a collapsed state, progressively revealing second electrical contacts (370) from behind accordion flap (388).

FIG. 17C shows second connector (368) in a fully seated position relative to first connector (362), when shaft assembly (14) has been fully seated with handle assembly (12). In this position, first and second electrical contacts (364, 370) electrically couple to establish an electrical connection between handle assembly (12) and shaft assembly (14). Simultaneously, first and second sealing portions (366, 372) sealingly engage to establish a liquid-tight seal that circumferentially surrounds the electrical connection and protects it from unwanted exposure to liquids that might otherwise cause electrical shorting. In particular, overhang feature (386) is received within upper opening (380) of first sealing portion (366) such that opposed lateral ends of overhang feature (386) span between and sealingly engage inner surfaces of side portions (374, 376) of first sealing element (366). Additionally, side portions (374, 376) of first sealing element (366) sealingly engage the side faces of projecting feature (382) as well as recessed side surfaces (384) of second connector (368). Further, a lower surface of projecting feature (382) sealingly engages lower portion (378) of first sealing element (366). As seen in FIG. 17C, accordion flap (388) compresses to establish a secondary sealing layer extending laterally across an upper side of the coupled electrical contacts (364, 370), thereby enhancing the liquid-tight seal. Upon subsequent detachment of shaft assembly (14) from handle assembly (12), accordion flap (388) may return to its expanded state to cover and protect second electrical contacts (370) from exposure to liquids.

H. Sealable Electrical Connection Assembly Having Sealing Teeth

Figure 18:
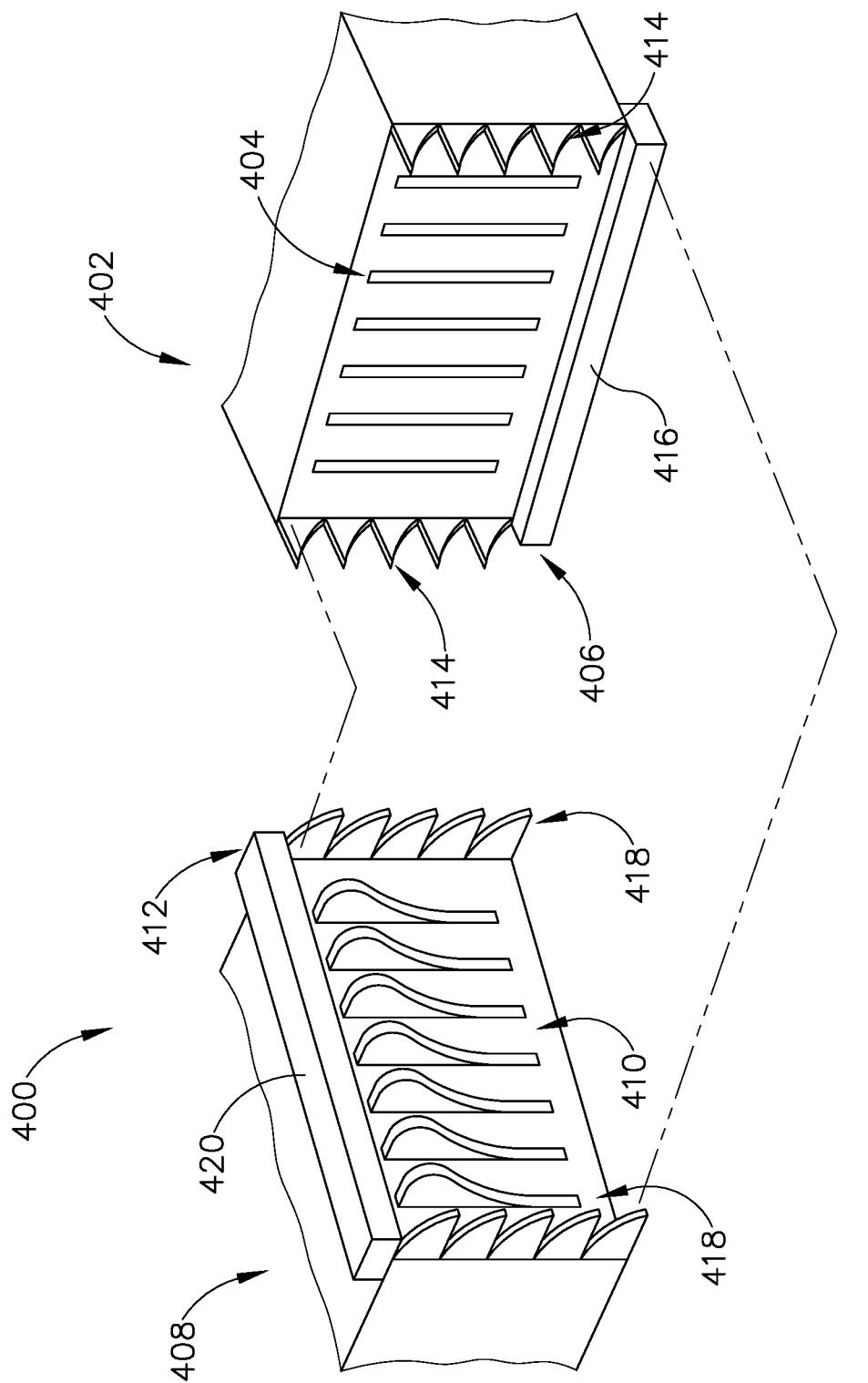
FIG. 18 depicts a schematic perspective view of another exemplary sealable electrical connection assembly suitable for use with the surgical instrument of FIG. 1, showing the first and second portions of the assembly in a disengaged state.

FIG. 18 shows another exemplary sealable electrical connection assembly (400) suitable for use with surgical instrument (10). Sealable electrical connection assembly (400) includes a first connector (402) that is supported by and is fixed relative to a distally facing portion of handle frame (26) of handle assembly (12). First connector (402) has a plurality of first electrical contacts (404) and a first sealing portion (406). Connection assembly (400) further includes a second connector (408) that is supported by and is fixed relative to a proximally facing portion of tool chassis (80) of shaft assembly (14). Second connector (408) has a plurality of second electrical contacts (410) and a second sealing portion (412). First electrical contacts (404) are in electrical communication with handle circuit board (46), and second electrical contacts (410) are in electrical communication with shaft circuit board (134). In other examples, a reverse configuration may be provided in which first connector (402) is coupled to shaft assembly (14) and second connector (408) is coupled to handle assembly (12).

Figure 19A:
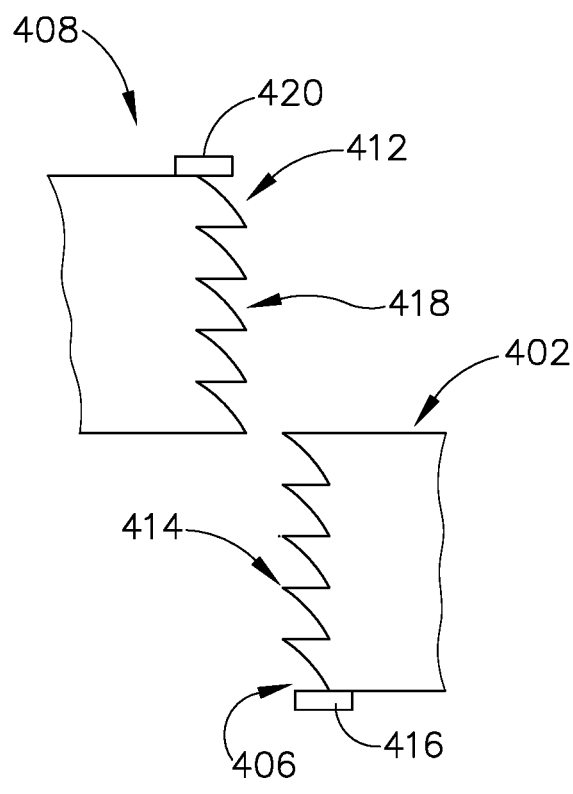
FIG. 19A depicts a side elevational view of the sealable electrical connection assembly of FIG. 18, showing the first and second portions in a disengaged state.

First sealing portion (406) of first connector (402) includes a first column of first teeth (414) arranged vertically along a first side of first electrical contacts (404), a second column of first teeth (414) arranged vertically along an opposed second side of first electrical contacts (404), and a lower sealing element (416) extending laterally along a lower side of first electrical contacts (404). Second sealing portion (412) of second connector (408) includes a first column of second teeth (418) arranged vertically along a first side of second electrical contacts (410), a second column of second teeth (418) arranged vertically along an opposed second side of second electrical contacts (410), and an upper sealing element (420) extending laterally along an upper side of second electrical contacts (410). As shown in FIG. 19A, lower sealing element (416) projects distally beyond a lower surface of first connector (402), and upper sealing element (420) projects proximally beyond an upper surface of second connector (408). In other versions, a reverse configuration may be provided in which first sealing portion (406) includes an upper sealing element and second sealing portion (412) includes a lower sealing element (416).

Figure 19B:
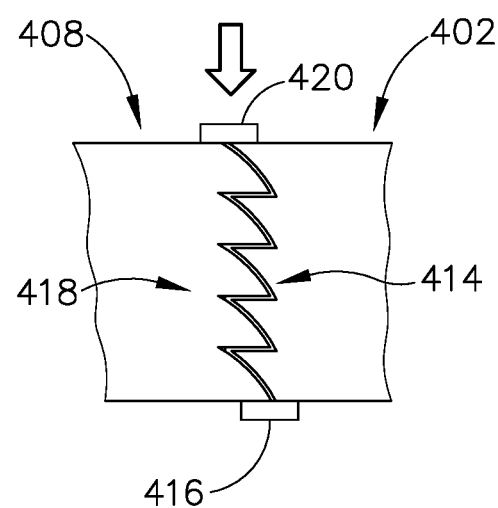
FIG. 19B depicts a side elevational view of the sealable electrical connection assembly of FIG. 19A, showing the first and second portions in an engaged state.

As shown in FIGS. 19A and 19B, first teeth (414) are formed with a first shape and second teeth (418) are formed with a complementary second shape. Additionally, teeth (414, 418) may be formed of a flexible elastomeric material, such as santoprene. Such a configuration enables teeth (414, 418) to resiliently deflect against one another and sealingly engage to establish a liquid-tight seal when first and second connectors (402, 408) are coupled together, as described below. Upper and lower sealing elements (416, 418) may be formed of a flexible elastomeric material as well.

FIG. 19A shows second connector (408) positioned vertically above first connector (402) as the proximal end of shaft assembly (14) is aligned with the distal end of handle assembly (12) along installation axis (IA). As shaft assembly (14) slides downwardly along installation axis (IA) into engagement with handle assembly (12), second connector (408) fully seats with first connector (402), as shown in FIG. 19B. In this position, first and second electrical contacts (404, 410) electrically couple to establish an electrical connection between handle assembly (12) and shaft assembly (14). Simultaneously, first teeth (414) of first connector (402) sealingly engage second teeth (418) of second connector (408). Additionally, upper sealing element (420) of second connector (408) overlaps and sealingly engages an upper surface of first connector (402), and lower sealing element (416) of first connector (402) overlaps and sealingly engages a lower surface of second connector. Accordingly, teeth (414, 418) and sealing elements (416, 420) cooperate to establish a liquid-tight seal that circumferentially surrounds the electrical connection and protects it from unwanted exposure to liquids that might otherwise cause electrical shorting.

I. Sealable Electrical Connection Assembly Having Trapezoidal Sealing Elements

Figure 20:
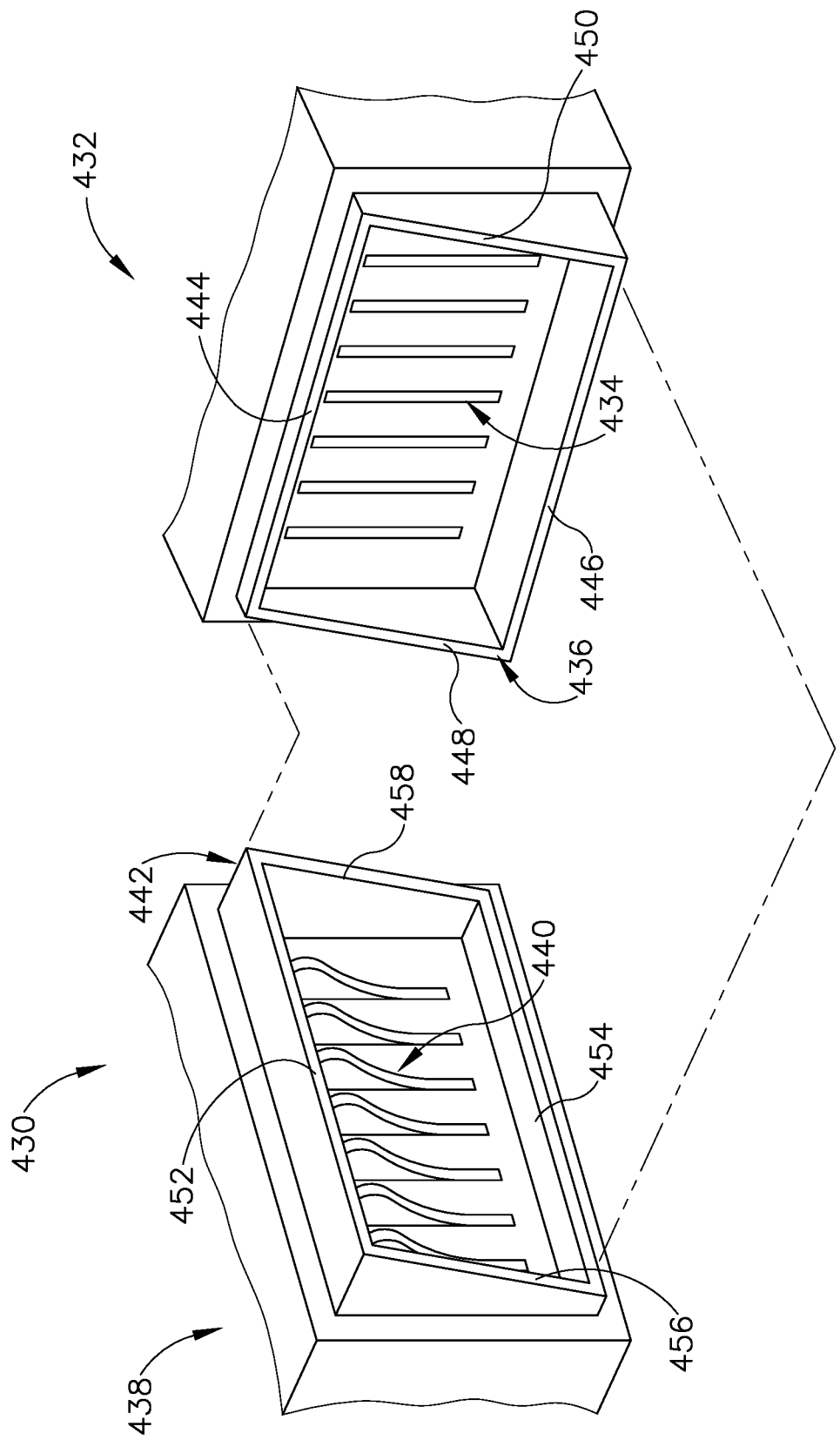
FIG. 20 depicts a schematic perspective view of another exemplary sealable electrical connection assembly suitable for use with the surgical instrument of FIG. 1, showing the first and second portions of the assembly in a disengaged state.

FIG. 20 shows another exemplary sealable electrical connection assembly (430) suitable for use with surgical instrument (10). Sealable electrical connection assembly (430) includes a first connector (432) that is supported by and is fixed relative to a distally facing portion of handle frame (26) of handle assembly (12). First connector (432) has a plurality of first electrical contacts (434) and a first sealing portion (436) that circumferentially surrounds first electrical contacts (434). Connection assembly (430) further includes a second connector (438) that is supported by and is fixed relative to a proximally facing portion of tool chassis (80) of shaft assembly (14). Second connector (438) has a plurality of second electrical contacts (440) and a second sealing portion (442) that circumferentially surrounds second electrical contacts (440). First electrical contacts (434) are in electrical communication with handle circuit board (46), and second electrical contacts (440) are in electrical communication with shaft circuit board (134). In other examples, a reverse configuration may be provided in which first connector (432) is coupled to shaft assembly (14) and second connector (438) is coupled to handle assembly (12).

First sealing portion (436) of the present example is in the form of first trapezoidal-shaped sealing element that projects distally and has a distally facing sealing surface that defines an upper lateral edge (444), an opposed lower lateral edge (446), a first angled side edge (448), and an opposed second angled side edge (450). Lower lateral edge (446) projects distally beyond upper lateral edge (444) so as to provide first sealing element (436) with its trapezoidal shape in a longitudinal plane. Second sealing portion (442) is shown in the form of a second trapezoidal-shaped sealing element that projects proximally and has a proximally facing sealing surface that defines an upper lateral edge (452), an opposed lower lateral edge (454), a first angled side edge (456), and an opposed second angled side edge (458). Upper lateral edge (452) projects proximally beyond lower lateral edge (454) so as to provide second sealing element (442) with a trapezoidal shape of complementary orientation to that of first sealing element (436), which promotes mating and sealing engagement as described below. Sealing elements (436, 442) may each be formed of a flexible elastomeric material, such as santoprene, for example.

Figures 21A, 21B:
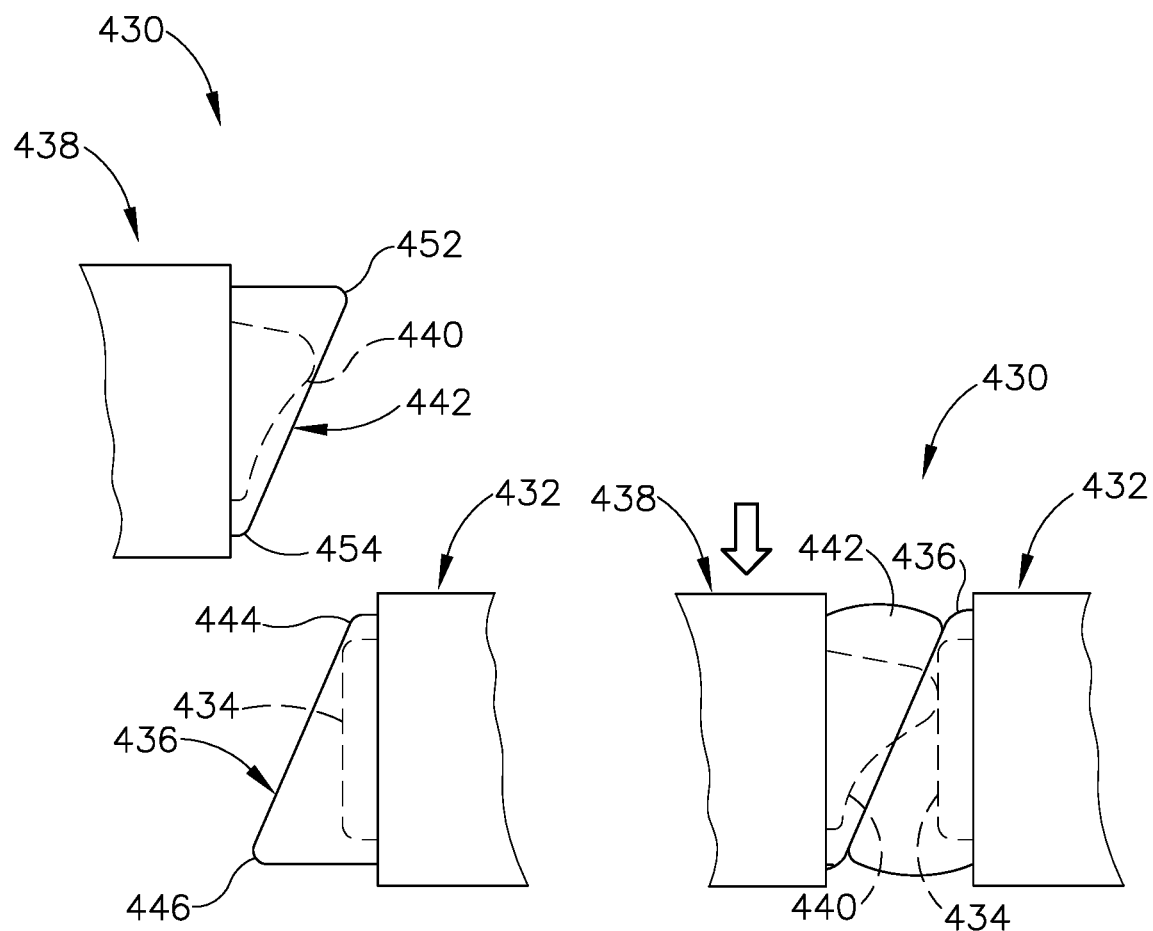
FIG. 21A depicts a side elevational view of the sealable electrical connection assembly of FIG. 20, showing the first and second portions in a disengaged state.
FIG. 21B depicts a side elevational view of the sealable electrical connection assembly of FIG. 20, showing the first and second portions in an engaged state.

FIG. 21A shows second connector (438) positioned vertically above first connector (432) as the proximal end of shaft assembly (14) is aligned with the distal end of handle assembly (12) along installation axis (IA). As shaft assembly (14) slides downwardly along installation axis (IA) into engagement with handle assembly (12), second connector (438) fully seats with first connector (432), as shown in FIG. 21B. In this position, first and second electrical contacts (434, 440) electrically couple to establish an electrical connection between handle assembly (12) and shaft assembly (14). Simultaneously, the distally facing surface of first sealing element (436) sealingly engages the proximally facing surface of second sealing element (442). This engagement establishes a liquid-tight seal that circumferentially surrounds the electrical connection and protects it from unwanted exposure to liquids that might otherwise cause electrical shorting.

The trapezoidal shaping of sealing elements (436, 442), provided by angled side edges (448, 450, 456, 458), promotes slight proximal compression of first sealing element (436) and slight distal compression of second sealing element (442) as their sealing surfaces slidably engage one another. Such compression promotes a secure liquid-tight seal between sealing elements (436, 442) when shaft assembly (14) is coupled to handle assembly (12). Furthermore, the trapezoidal shapes of sealing elements (436, 442) increases the area of their sealing surfaces, thereby enhancing the liquid-tight seal. As seen in FIG. 21B, the resulting liquid-tight seal defines a seal plane that extends obliquely relative to the longitudinal axis of shaft assembly (14).

Figure 22:
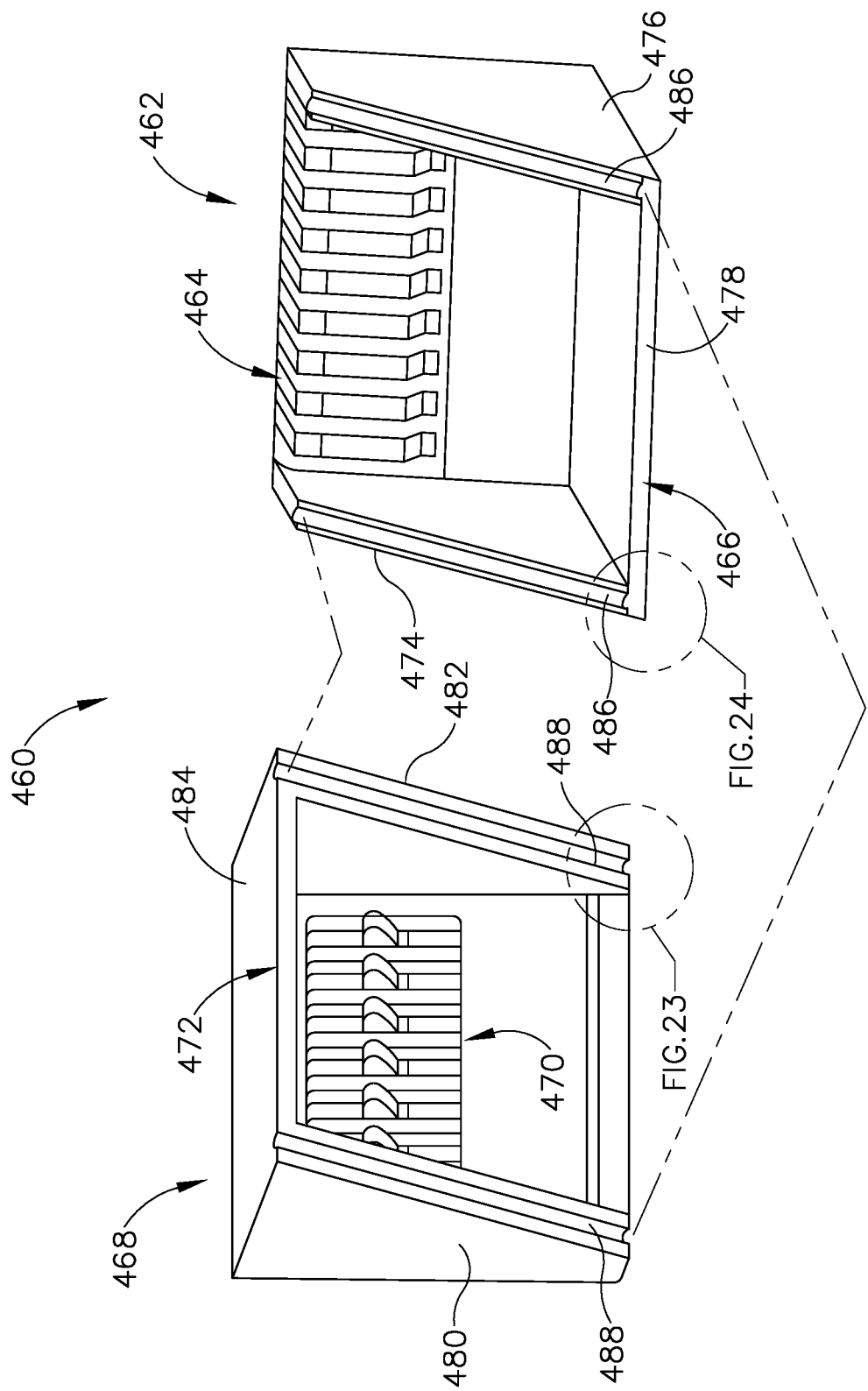
FIG. 22 depicts a perspective view of another exemplary sealable electrical connection assembly suitable for use with the surgical instrument of FIG. 1, showing the first and second portions of the assembly in a disengaged state.

J. Sealable Electrical Connection Assembly Having Trapezoidal Sealing Elements with Interlocking Features FIG. 22 shows another exemplary sealable electrical connection assembly (460) suitable for use with surgical instrument (10). Sealable electrical connection assembly (460) includes a first connector (462) that is supported by and is fixed relative to a distally facing portion of handle frame (26) of handle assembly (12). First connector (462) has a plurality of first electrical contacts (464) and a first sealing portion (466). Connection assembly (460) further includes a second connector (468) that is supported by and is fixed relative to a proximally facing portion of tool chassis (80) of shaft assembly (14). Second connector (468) has a plurality of second electrical contacts (470) and a second sealing portion (472). First electrical contacts (464) are in electrical communication with handle circuit board (46), and second electrical contacts (470) are in electrical communication with shaft circuit board (134). In other examples, a reverse configuration may be provided in which first connector (462) is coupled to shaft assembly (14) and second connector (468) is coupled to handle assembly (12).

First sealing portion (466) is shown in the form first trapezoidal-shaped sealing element that projects distally from handle assembly (12). First trapezoidal sealing element (466) includes a first trapezoidal sidewall (474) extending vertically along a first side of first electrical contacts (464), an opposed second trapezoidal sidewall (476) extending vertically along an opposed second side of first electrical contacts (464), and a lower wall (478) extending laterally between first and second trapezoidal sidewalls (474, 476) along a lower side of first electrical contacts (464). In some versions, first sealing element (466) may further include an upper wall extending laterally along an upper side of first electrical contacts (464). Distal ends of walls (474, 476, 478) define a distally facing sealing surface.

Second sealing portion (472) is shown in the form of a second trapezoidal-shaped sealing element that projects proximally from shaft assembly (14). Second trapezoidal sealing element (472) includes a first trapezoidal sidewall (480) extending vertically along a first side of second electrical contacts (470), an opposed second trapezoidal sidewall (482) extending vertically along an opposed second side of second electrical contacts (470), and an upper wall (484) extending laterally between first and second trapezoidal sidewalls (480, 482) along an upper side of second electrical contacts (470). In some versions, second sealing element (472) may further include a lower wall extending laterally along a lower side of second electrical contacts (470). Proximal ends of walls (480, 482, 484) define a proximally facing sealing surface configured to sealingly engage the distal sealing surface of first sealing element (466).

As shown in FIG. 22, first sealing element (466) is provided with a first trapezoidal orientation in which a lower end of first sealing element (466) extends distally beyond its upper end. By comparison, second sealing element (472) is provided with a complementary second trapezoidal orientation in which an upper end of second sealing element (472) extends proximally beyond its lower end. This complementary configuration promotes sealing engagement of first and second sealing elements (466, 472) in a manner similar to trapezoidal sealing elements (436, 442) described above.

Figure 23:
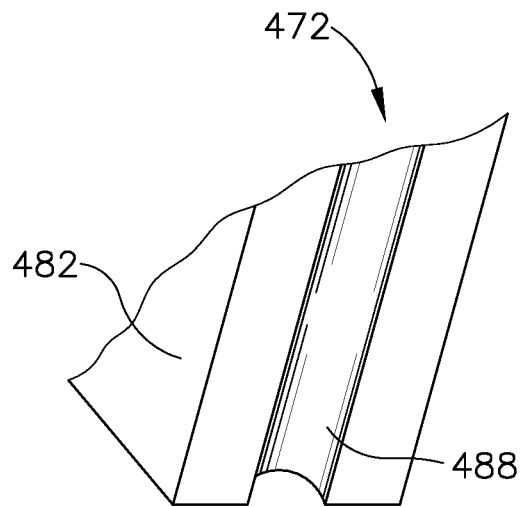
FIG. 23 depicts an enlarged perspective view of an interlocking feature of the second portion of the sealable electrical connection assembly of FIG. 22.
Figure 24:
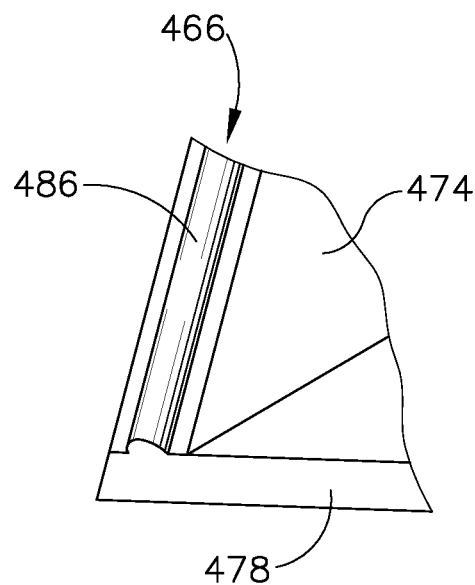
FIG. 24 depicts an enlarged perspective view of an interlocking feature of the first portion of the sealable electrical connection assembly of FIG. 22.
Figure 25:
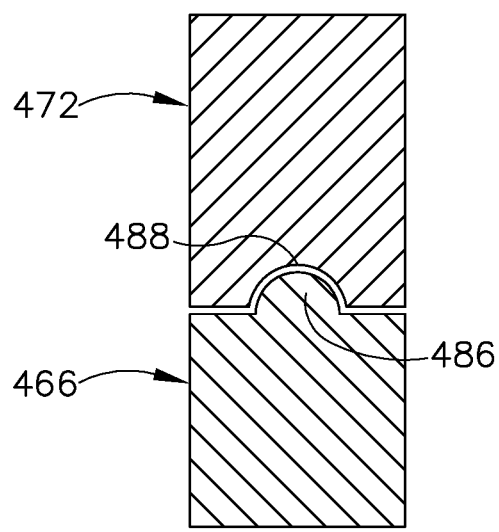
FIG. 25 depicts a top-down sectional view of the interlocking features of the first and second portions of the sealable electrical connection assembly of FIG. 22, showing the interlocking features in an interlocked state.

As shown best in FIGS. 23-25, first and second trapezoidal sealing elements (466, 472) include complementary features configured to lockingly engage one another when shaft assembly (14) is attached to handle assembly (12). In the present example, the distal end of each trapezoidal sidewall (474, 476) of first sealing element (466) includes a linear rail (486). The proximal end of each trapezoidal sidewall (480, 482) of second sealing element (472) includes a linear groove (488) configured to receive a respective one of linear rails (486) in an interlocking, snap-fit engagement, as shown in FIG. 25. In other examples, a reverse configuration may be provided in which rails (486) are formed on second sealing element (472) and grooves (488) are formed on first sealing element (466). As shown in FIG. 25, grooves (488) have a concave profile while rails (486) have a complementary convex profile.

To promote interlocking engagement between rails (486) and grooves (488), rails (486) may be formed of a rigid first material while grooves (488) are formed of a more flexible second material that promotes resilient deformation of grooves (488) to accommodate rails (486). For instance, second sealing element (472), including the structure defining grooves (488), may be formed of a flexible elastomeric material, such as santoprene, while first sealing element (466) is formed of a more rigid material. In other examples, first sealing element (466), including the structure defining rails (486), may be formed of a flexible elastomeric material, while second sealing element (472) is formed of a more rigid material. In other examples, both sealing elements (466, 472) may be formed of a similar flexible elastomeric material.

As the proximal end of shaft assembly (14) is attached to the distal end of handle assembly (12) along installation axis (IA), first electrical contacts (464) of first connector (462) are brought into electrical engagement with second electrical contacts (470) of second connector (468), such that an electrical connection is formed therebetween. Simultaneously, the distal end of first trapezoidal sealing element (466) engages the proximal end of second trapezoidal sealing element (472), causing sealing elements (466, 472) to compress against one another in a manner similar to that described above in connection with trapezoidal sealing elements (436, 442). This compression causes rails (486) of first sealing element (466) to interlock with grooves (488) of second sealing element (472), such that trapezoidal sidewalls (474, 476, 480, 482) of sealing elements (466, 472) sealingly engage one another. Simultaneously, lower wall (478) of first sealing element (466) may sealingly engage an opposed proximally-facing surface of shaft assembly (14), while upper wall (484) of second sealing element (472) sealingly engages an opposed distally-facing surface of handle assembly (12). In this manner, first and second connectors (462, 468) establish a liquid-tight seal that circumferentially surrounds the electrical connection and protects it from unwanted exposure to liquids that might otherwise cause electrical shorting. Similar to connection assembly (430) described above, the resulting liquid-tight seal defines a seal plane that extends obliquely relative to the longitudinal axis of shaft assembly (14).

Similar to trapezoidal sealing elements (436, 442) described above, trapezoidal sealing elements (466, 472) of the present example exhibit the benefit of providing sealing surfaces of increased surface area. Further, the interlocking features of sealing elements (466, 472) provide additional stability to the liquid-tight seal, and enhanced protection for the electrical connection formed between first and second electrical contacts (462, 468).

Figure 26:
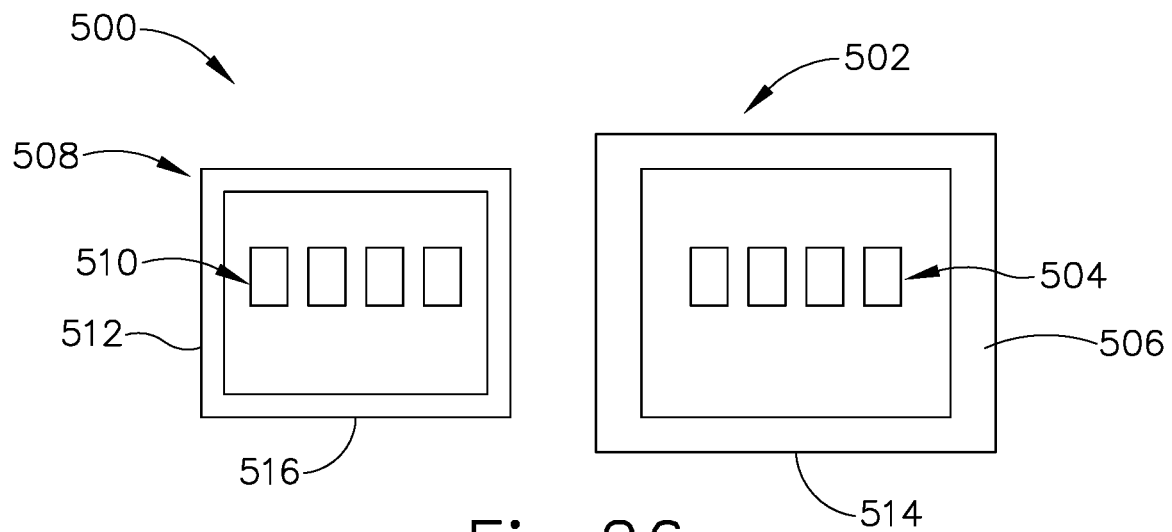
FIG. 26 depicts a schematic front elevational view of first and second portions of another exemplary sealable electrical connection assembly suitable for use with the surgical instrument of FIG. 1, showing the first and second portions in a disengaged state.
Figure 27:
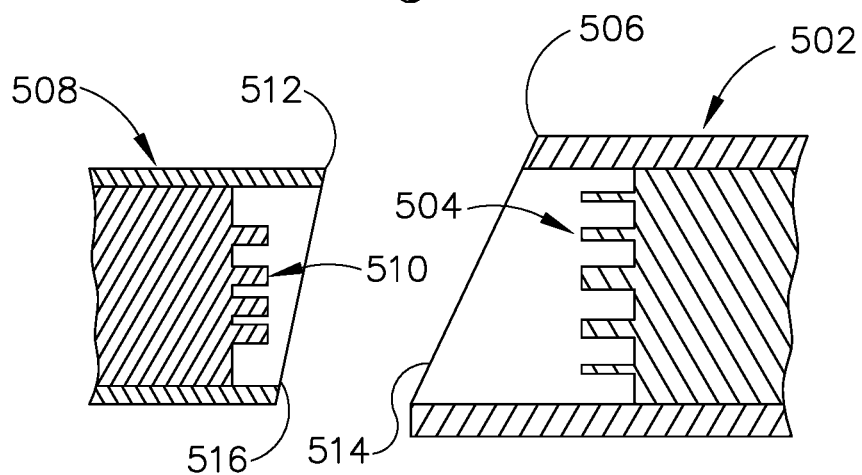
FIG. 27 depicts a schematic top-down cross-sectional view of the sealing electrical connection assembly of FIG. 26, showing the first and second portions in a disengaged state.
Figure 28:
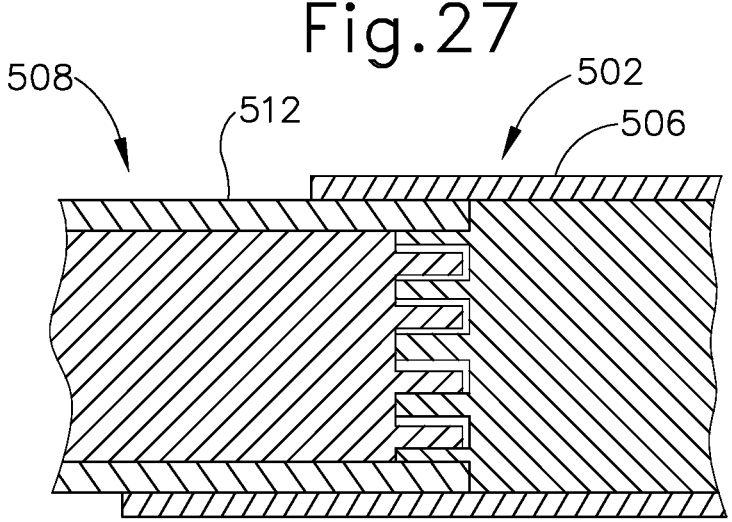
FIG. 28 depicts another schematic top-down cross-sectional view of the sealing electrical connection assembly of FIG. 26, showing the first and second portions in an engaged state.

K. Sealable Electrical Connection Assembly Having Axially Overlapping Sealing Elements FIGS. 26-28 show another exemplary sealable electrical connection assembly (500) suitable for use with surgical instrument (10). Sealable electrical connection assembly (500) includes a first connector (502) that is supported by and is fixed relative to a distally facing portion of handle frame (26) of handle assembly (12). First connector (502) has a plurality of first electrical contacts (504) and a first sealing portion (506) that circumferentially surrounds first electrical contacts (504). Connection assembly (500) further includes a second connector (508) that is supported by and is fixed relative to a proximally facing portion of tool chassis (80) of shaft assembly (14). Second connector (508) has a plurality of second electrical contacts (510) and a second sealing portion (512) that circumferentially surrounds second electrical contacts (510). First electrical contacts (504) are in electrical communication with handle circuit board (46), and second electrical contacts (510) are in electrical communication with shaft circuit board (134). In other examples, a reverse configuration may be provided in which first connector (502) is coupled to shaft assembly (14) and second connector (508) is coupled to handle assembly (12).

First sealing portion (506) of first connector (502) is shown in the form of a first sealing element that projects distally from handle assembly (12) and circumferentially surrounds first electrical contacts (504). Second sealing portion (512) of second connector (508) is shown in the form of a second sealing element that projects proximally from shaft assembly (14) and circumferentially surrounds second electrical contacts (510). As shown best in FIG. 27, first sealing element (506) has an angled distal end (514) that provides first sealing element (506) with a first trapezoidal shape in a laterally extending plane. Second sealing element (512) has an angled proximal end (516) that provides second sealing element (512) with a second trapezoidal shape that generally complements the first trapezoidal shape of first sealing element (506).

As seen in FIGS. 26-28, second sealing element (512) is suitably sized to be inserted into first sealing element (506) when shaft assembly (14) is attached to handle assembly (12). In particular, second sealing element (472) is formed with a width and height, in directions transverse to the longitudinal axis of shaft assembly (14), that are less than a corresponding width and height of first sealing element (506). In other examples, a reverse configuration may be provided in which first sealing element (506) is sized to be inserted into second sealing element (512). Sealing elements (506, 512) may each be formed of a flexible elastomeric material, such as santoprene for example, that enables sealing elements (506, 512) to resiliently deform as second sealing element (512) is received within first sealing element (506) when shaft assembly (14) is attached to handle assembly (12).

FIG. 28 shows engagement of first and second connectors (502, 508) when shaft assembly (14) is attached to handle assembly (12) along installation axis (IA). First electrical contacts (504) engage second electrical contacts (510) to establish an electrical connection therebetween. Simultaneously, the sidewalls of first and/or second sealing elements (506, 512) resiliently deform to permit second sealing element (512) to be received within first sealing element (506), along installation axis (IA). Angled ends (514, 516) of sealing elements (506, 512) may also facilitate insertion of second sealing element (512) into first sealing element (506). This engagement of sealing elements (506, 512) yields a liquid-tight seal therebetween that circumferentially surrounds the electrical connection and protects it from unwanted exposed to liquids.

As seen in FIG. 28, the resulting axial overlap of sealing elements (506, 512) provides the liquid-tight seal with first and second layers rather than a single layer, thereby providing enhanced protection against fluid ingress. In other versions, one of sealing elements (506, 512) may be omitted, such that connection assembly (500) includes a single axially-extending sealing element that is configured to sealingly engage an opposing surface of handle assembly (12) or shaft assembly (14) and thereby establish a liquid-tight seal that circumferentially surrounds the electrical connection with a single layer of elastomeric material.

III. Exemplary Fluid Path Configurations for Draining Fluid from Electrical Connection In some instances, it may be desirable to provide surgical instrument (10) with features that facilitate drainage of fluids from the interface between shaft assembly (14) and handle assembly (12), for example to protect against shorting of the electrical connection between handle and shaft assemblies (12, 14). Various exemplary configurations of such features are described below. Each such configuration provides at least one fluid passageway having a diameter that is sufficiently small to draw fluid away from the electrical connection and toward an exterior of surgical instrument (10) via capillary action. It will be understood that such features may be provided in combination with, or independently from, any one or more of the exemplary sealable electrical connection assemblies described above. Moreover, any one or more of the exemplary configurations described below may be employed in combination with each other.

Figure 29:
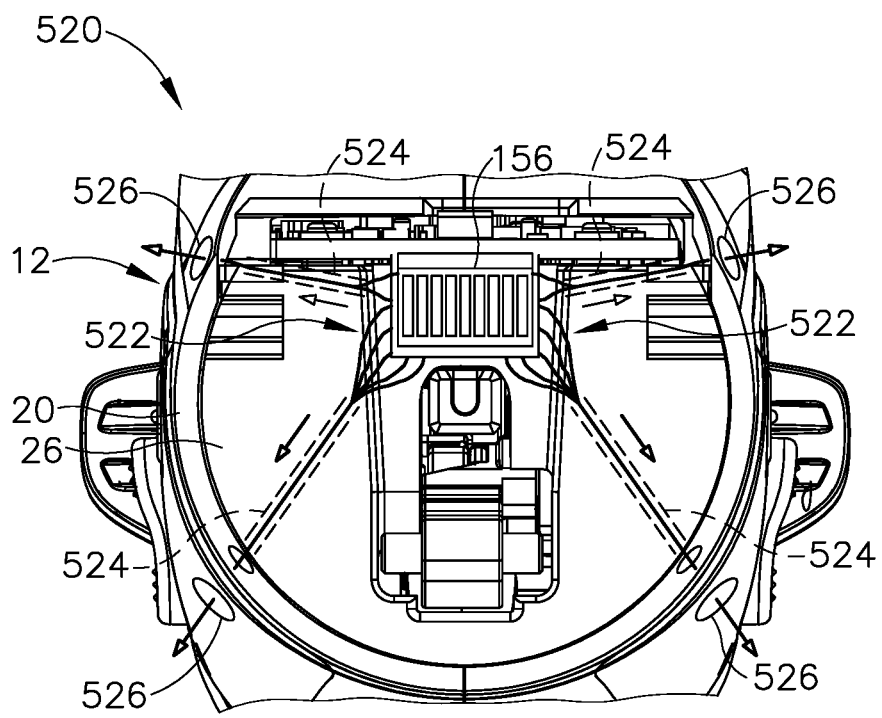
FIG. 29 depicts a schematic front elevational view of the distal end of the handle assembly of the surgical instrument of FIG. 1 having an exemplary configuration of fluid paths for directing fluid away from an electrical connection of the instrument.

FIG. 29 shows a first exemplary configuration (520) of features configured to direct fluid away from the electrical connection between handle assembly (12) and shaft assembly (14). In the present example, handle frame (26) includes a plurality of capillary passageways (522) extending radially outward from handle electrical connector (156) and toward an exterior of handle assembly (12). Each capillary passageway (522) feeds into a drain channel (524) formed in handle frame (26) and which opens to an exterior of handle body (20) via a weep hole (526). In the present example, handle assembly (12) includes four drain channels (524) extending angularly outwardly from respective corners of electrical connector (156). Various other quantities and arrangements of capillary passageways, drain channels (524), and weep holes (526) may be provided in other versions.

Capillary passageways (522), drain channels (524), and weep holes (526) may be formed entirely in the structure of handle assembly (12), or by handle assembly (12) and shaft assembly (14) in combination when assembled. For instance, handle assembly (12) may define a first half of each capillary passageway (522), drain channel (524), and/or weep hole (526), and shaft assembly (14) may define a second half of each capillary passageway (522), drain channel (524), and/or weep hole (526). It will be appreciated that similar methods of construction may be applied to any of the other exemplary configurations (530, 540, 550, 570, 580) described below.

Figure 30:
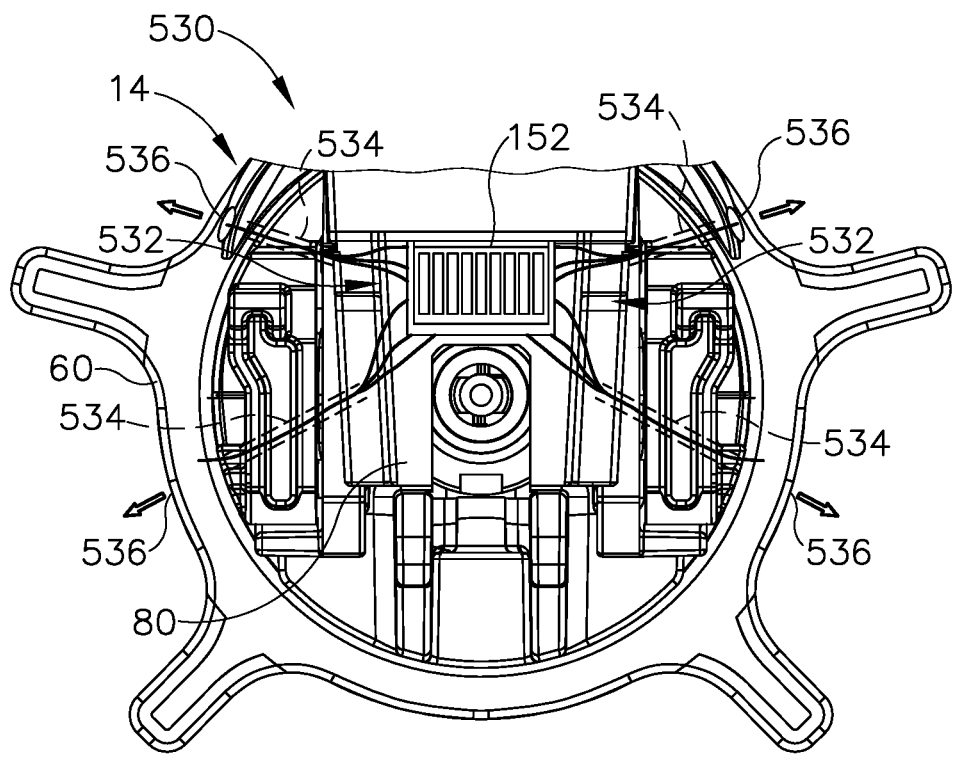
FIG. 30 depicts a schematic front elevational view of the proximal end of the shaft assembly of the surgical instrument of FIG. 1 having an exemplary configuration of fluid paths for directing fluid away from an electrical connection of the instrument.

FIG. 30 shows another exemplary configuration (530) of features configured to direct fluid away from the electrical connection between handle assembly (12) and shaft assembly (14). In the present example, tool chassis (80) of shaft assembly (14) includes a plurality of capillary passageways (532) extending radially outward from shaft electrical connector (152) and toward an exterior of nozzle (60). Each capillary passageway (532) feeds into a drain channel (534) formed in tool chassis (80) and which opens to an exterior of nozzle (60) via a weep hole (536). In the present example, handle assembly (12) includes four drain channels (534) extending angularly outwardly from respective corners of electrical connector (152). In other versions, various other quantities and arrangements of capillary passageways (532), drain channels (534), and weep holes (536) may be provided.

Figure 31:
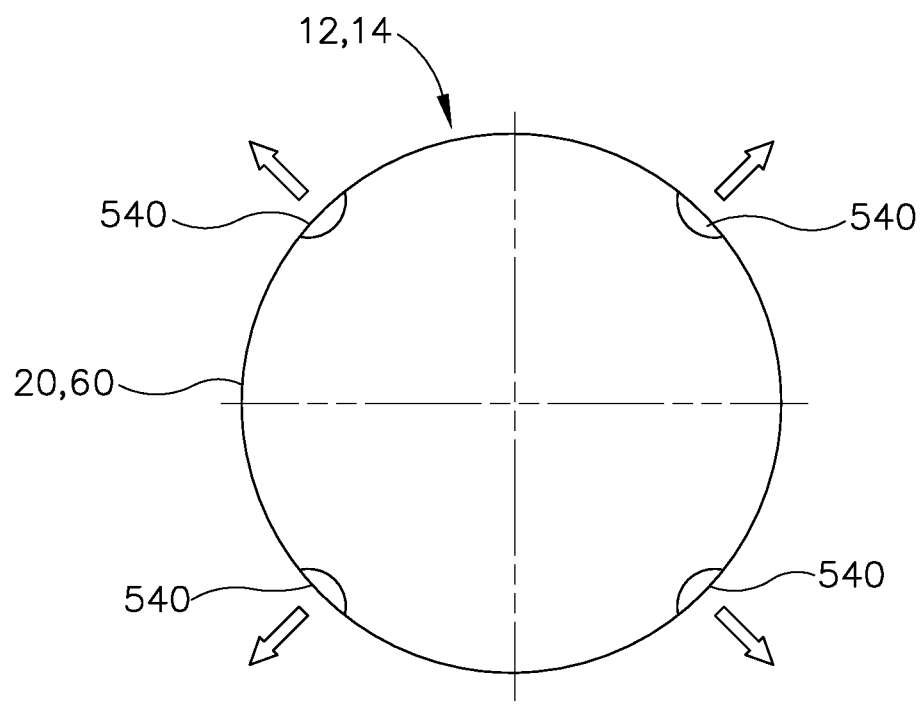
FIG. 31 depicts a schematic end view of a distal end of the handle assembly or alternatively a proximal end of the shaft assembly of the surgical instrument of FIG. 1, having an exemplary configuration of weep holes for draining fluid away from an electrical connection of the device.

FIG. 31 is a schematic view showing an exemplary arrangement of weep holes (540) formed at or near the interface between handle assembly (12) and shaft assembly (14). Each weep hole (540) communicates with a respective drain channel (not shown), such as one of drain channels (524, 534) described above, and is configured to expel fluid to an exterior of surgical instrument (10) to thereby prevent against shorting of the electrical connection formed between handle assembly (12) and shaft assembly (14) when assembled. In the present example, four weep holes (540) are provided at uniform circumferential spacing of approximately 90 degrees, with each weep hole (540) positioned at approximately 45 degrees from horizontal in its respective quadrant. Such an arrangement ensures adequate drainage of fluids from electrical connector (152, 156) in any direction. In other examples, however, other quantities and arrangements of weep holes (540) may be provided.

Figure 32:
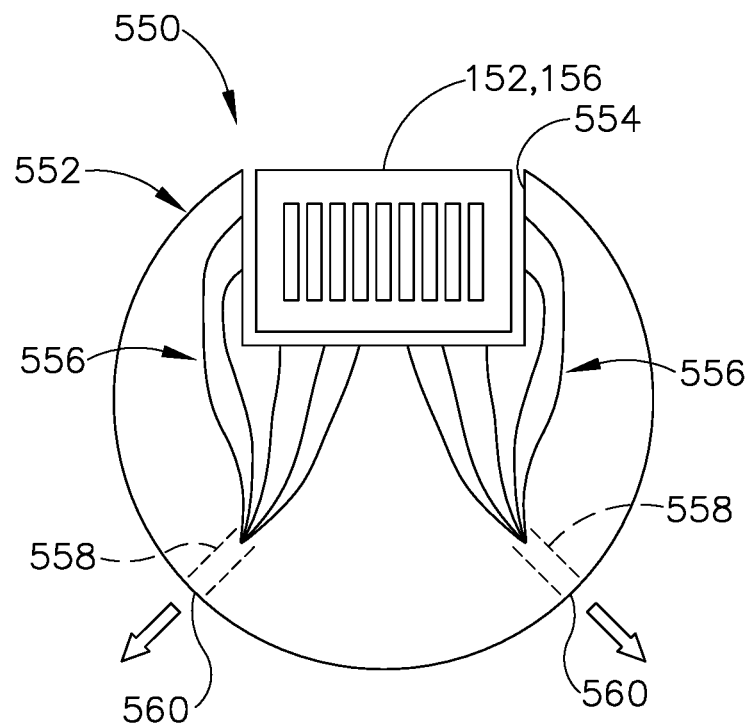
FIG. 32 depicts a schematic end view of a distal end of the handle assembly or alternatively a proximal end of the shaft assembly of the surgical instrument of FIG. 1, having another exemplary configuration of fluid paths for directing fluid away from an electrical connection of the instrument.

FIG. 32 shows another exemplary configuration (550) of features configured to direct fluid away from the electrical connection between handle assembly (12) and shaft assembly (14). Configuration (550) includes a disc structure (552) that is suitable for use with handle assembly (12) or shaft assembly (14), and which is configured to abut handle frame (26) and/or tool chassis (80) in use. Disc structure (552) includes an upper cutout feature (554) configured to accommodate the respective electrical connector (152, 156), a plurality of capillary passageways (556) extending downwardly and away from cutout feature (554), and a pair of drain channels (558) into which capillary passageways (556) feed. Each drain channel (558) is configured to expel fluids to an exterior of surgical instrument (10) through a respective weep hole (560).

Figure 33:
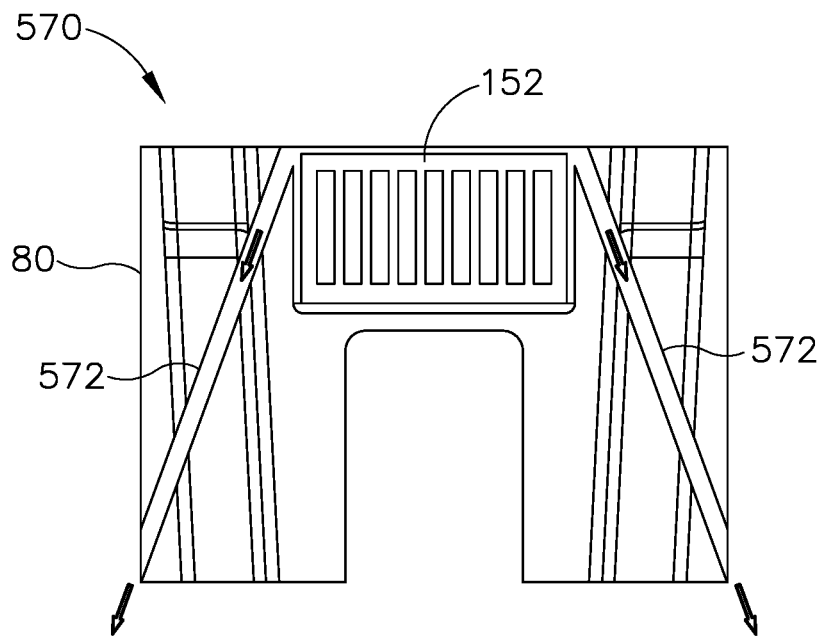
FIG. 33 depicts a schematic front elevational view of a proximal end of a support structure of the shaft assembly of the surgical instrument of FIG. 1, having an exemplary configuration of fluid paths for directing fluid away from an electrical connection of the instrument.

FIG. 33 shows another exemplary configuration (570) of features configured to direct fluid away from the electrical connection between handle assembly (12) and shaft assembly (14). In the present example, tool chassis (80) includes a pair of capillary passageways (572) that originate at upper corners of shaft electrical connector (152) and extend angularly downward. Passageways (572) extend toward and exit to an exterior of shaft assembly (14) through a pair of weep holes (not shown). This configuration ensures drainage of fluids from the electrical connection between handle assembly (12) and shaft assembly (14) before such fluids reach the electrical connection. In some versions, similar features may be provided on handle assembly (12).

Figure 34:
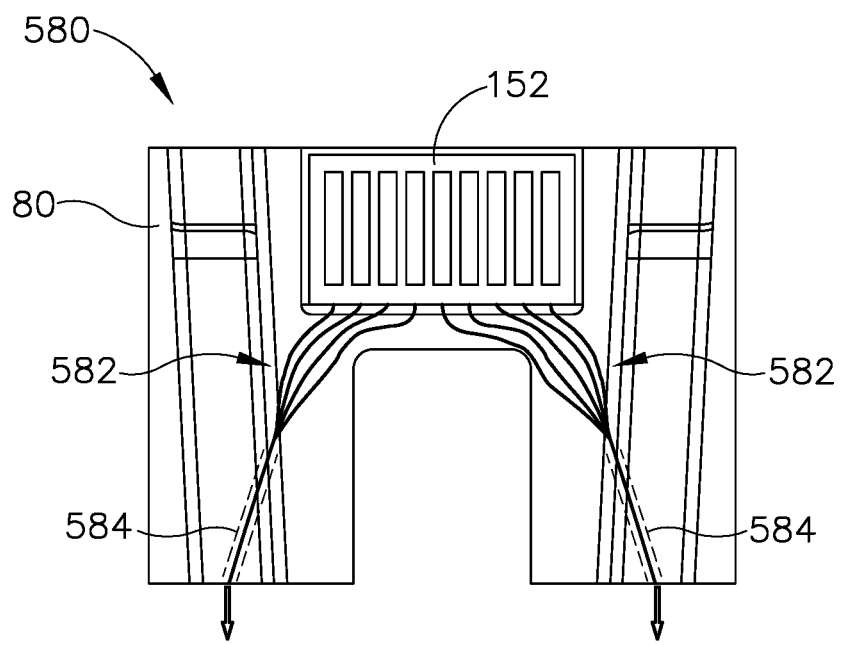
FIG. 34 depicts a schematic front elevational view of a proximal end of a support structure of the shaft assembly of the surgical instrument of FIG. 1, having another exemplary configuration of fluid paths for directing fluid away from an electrical connection of the instrument.

FIG. 34 shows another exemplary configuration (580) of features configured to direct fluid away from the electrical connection between handle assembly (12) and shaft assembly (14). In the present example, tool chassis (80) includes a plurality of capillary passageways (582) that originate at a lower side of shaft electrical connector (152). Each capillary passageway (582) aligns with a respective electrical contact of electrical connector (152), such that the natural fluid channel defined by the electrical contact couples with the respective capillary passageway (582). Each capillary passageway (582) extends downwardly from connector (152) and feeds into one of two drain channels (584) that open to an exterior of surgical instrument (10) through respective weep holes (not shown). In some versions, similar features may be provided on handle assembly (12).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body assembly, wherein the body assembly includes: (i) a first electrical contact, and (ii) a first sealing portion; (b) a shaft assembly, wherein the shaft assembly is configured to releasably attach to and extend distally from the body assembly, wherein the shaft assembly includes: (i) a second electrical contact, and (ii) a second sealing portion; and (c) an end effector at a distal end of the shaft assembly, wherein the end effector is operable to treat tissue, wherein the first and second electrical contacts are configured to electrically couple together to establish an electrical connection therebetween when the shaft assembly is attached to the body assembly, wherein the first and second sealing portions are configured to sealingly engage one another when the shaft assembly is attached to the body assembly to establish a liquid-tight seal that surrounds the electrical connection.

Example 2

The surgical instrument of Example 1, wherein the first sealing portion is provided on a distal portion of the body assembly, wherein the second sealing portion is provided on a proximal portion of the shaft assembly.

Example 3

The surgical instrument of any of the preceding Examples, wherein the first and second sealing portions are each formed of an elastomeric material.

Example 4

The surgical instrument of any of the preceding Examples, wherein the shaft assembly defines a longitudinal axis, wherein the first and second sealing portions define a seal plane that extends transversely to the longitudinal axis.

Example 5

The surgical instrument of any of the preceding Examples, wherein the first sealing portion is configured to define first and second sides of the liquid-tight seal, wherein the second sealing portion is configured to define third and fourth sides of the liquid-tight seal.

Example 6

The surgical instrument of any of the preceding Examples, wherein the first sealing portion comprises a first pair of sealing elements that define opposed first and second sides of the liquid-tight seal, wherein the second sealing portion comprises a second pair of sealing elements that define opposed third and fourth sides of the liquid-tight seal.

Example 7

The surgical instrument of any of the preceding Examples, wherein the first and second sealing portions are configured to cooperate to define a liquid-tight seal having a first side, a second side opposed from the first side, a third side, and a fourth side opposed from the third side, wherein one of the first or second sealing portions is configured to define the first, second, and third sides, wherein the other of the first or second sealing portions is configured to define the fourth side.

Example 8

The surgical instrument of any of the preceding Examples, wherein one of the first or second sealing portions has a U shape defining an opening, and other of the first or second sealing portions has a linear shape configured to close the opening when the shaft assembly is attached to the body assembly.

Example 9

The surgical instrument of any of the preceding Examples, wherein the second sealing portion comprises a wiper, wherein the wiper is configured to contact and wipe liquid from the first electrical contact during attachment of the shaft assembly to the body assembly.

Example 10

The surgical instrument of any of the preceding Examples, wherein the first sealing portion includes a lower opening configured to promote drainage of liquid from the first electrical contact during attachment of the shaft assembly to the body assembly.

Example 11

The surgical instrument of any of the preceding Examples, wherein at least one of the first sealing portion or the second sealing portion includes an accordion flap.

Example 12

The surgical instrument of any of the preceding Examples, wherein the first sealing portion includes a first trapezoidal feature and the second sealing portion includes a second trapezoidal feature configured to mate with the first trapezoidal feature.

Example 13

The surgical instrument of any of the preceding Examples, wherein the first sealing element circumferentially surrounds the first electrical contact, wherein the second sealing element circumferentially surrounds the second electrical contact.

Example 14

The surgical instrument of any of the preceding Examples, wherein the first sealing portion includes a first interlocking feature and the second sealing portion includes a second interlocking feature configured to interlock with the first interlocking feature when the shaft assembly is attached to the body assembly.

Example 15

The surgical instrument of any of the preceding Examples, wherein the first sealing portion includes a plurality of first teeth, wherein the second sealing portion includes a plurality of second teeth configured to sealingly engage the first teeth when the shaft assembly is attached to the body assembly.

Example 16

A surgical instrument, comprising: (a) a body assembly, wherein the body assembly includes a first electrical connector; (b) a shaft assembly defining a longitudinal axis, wherein the shaft assembly is configured to slide into engagement with the body assembly along an installation axis that extends transversely to the longitudinal axis, wherein the shaft assembly includes a second electrical connector configured to establish an electrical connection with the first electrical connector when the shaft assembly attaches to the body assembly; (c) a sealing layer disposed between the shaft assembly and the body assembly, wherein the sealing layer is configured to establish a liquid-tight seal that surrounds the electrical connection when the shaft assembly is attached to the body assembly; and (d) an end effector at a distal end of the shaft assembly, wherein the end effector is operable to treat tissue.

Example 17

The surgical instrument of Example 16, wherein the sealing layer defines a seal plane that extends parallel to the installation axis.

Example 18

The surgical instrument of any of Examples 16 through 17, wherein the sealing layer comprises a first sealing portion disposed on a distal portion of the body assembly, and a second sealing portion disposed on a proximal portion of the shaft assembly, wherein the first and second sealing portions are configured to cooperate to establish the liquid-tight seal when the shaft assembly is attached to the body assembly.

Example 19

A surgical instrument, comprising: (a) a body assembly, wherein the body assembly includes: (i) a first electrical contact, and (ii) a first sealing portion; (b) a shaft assembly, wherein the shaft assembly is configured to releasably attach to and extend distally from the body assembly, wherein the shaft assembly includes: (i) a second electrical contact, and (ii) a second sealing portion; and (c) an end effector at a distal end of the shaft assembly, wherein the end effector is operable to treat tissue, wherein the first and second electrical contacts are configured to electrically couple together to establish an electrical connection therebetween when the shaft assembly is attached to the body assembly, wherein the first sealing portion is configured to sealingly engage a portion of the shaft assembly and the second sealing portion is configured to sealingly engage a portion of the body assembly to thereby establish a liquid-tight seal that surrounds the electrical connection when the shaft assembly is attached to the body assembly.

Example 20

The surgical instrument of Example 19, wherein the first and second sealing portions are configured to cooperate to define a liquid-tight seal having a first side, a second side opposed from the first side, a third side, and a fourth side opposed from the third side, wherein one of the first or second sealing portions is configured to define the first, second, and third sides, wherein the other of the first or second sealing portions is configured to define the fourth side.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/934,139, entitled "Surgical Instrument With Compressible Electrical Connector," filed on Mar. 23, 2018, published as U.S. Pub. No. 2019/0290307 on Sep. 26, 2019; U.S. application Ser. No. 15/934,160, entitled "Surgical Instrument with Recessed Contacts and Electrically Insulting Barriers," filed on Mar. 23, 2018, published as U.S. Pub. No. 2019/0290269 on Sep. 26, 2019; U.S. application Ser. No. 15/934,166, entitled "Surgical Instrument with Electrical Contact Under Membrane," filed on Mar. 23, 2018, issued as U.S. Pat. No. 10,631,860 on Apr. 28, 2020; U.S. application Ser. No. 15/934,173, entitled "Staple Cartridge with Short Circuit Prevention Features," filed on Mar. 23, 2018, issued as U.S. Pat. No. 10,639,038 on May 5, 2020; U.S. application Ser. No. 15/934,180, entitled "Surgical Instrument with Capacitive Electrical Interface," filed on Mar. 23, 2018, published as U.S. Pub. No. 2019/0290272 on Sep. 26, 2019; and U.S. application Ser. No. 15/934,190, entitled "Slip Ring Assembly for Surgical Instrument," filed on Mar. 23, 2018, issued as U.S. Pat. No. 10,631,861 on Apr. 28, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
    (a) a body assembly, wherein the body assembly includes:
        (i) a first electrical contact, and
        (ii) a first sealing portion provided on a distal portion of the body assembly;
    (b) a shaft assembly, wherein the shaft assembly is configured to releasably attach to and extend distally from the body assembly, wherein the shaft assembly includes:
        (i) a second electrical contact, and
        (ii) a second sealing portion provided on a proximal portion of the shaft assembly; and
    (c) an end effector at a distal end of the shaft assembly, wherein the end effector is operable to treat tissue,
    wherein the first and second electrical contacts are configured to electrically couple together to establish an electrical connection therebetween when the shaft assembly is attached to the body assembly,
    wherein the first and second sealing portions are configured to sealingly engage one another when the shaft assembly is attached to the body assembly to establish a liquid-tight seal that surrounds the electrical connection.

2. The surgical instrument of claim 1, wherein the first and second sealing portions are each formed of an elastomeric material.

3. The surgical instrument of claim 1, wherein the shaft assembly defines a longitudinal axis, wherein the first and second sealing portions define a seal plane that extends transversely to the longitudinal axis.

4. The surgical instrument of claim 1, wherein the first sealing portion is configured to define first and second sides of the liquid-tight seal, wherein the second sealing portion is configured to define third and fourth sides of the liquid-tight seal.

5. The surgical instrument of claim 1, wherein the first sealing portion comprises a first pair of sealing elements that define opposed first and second sides of the liquid-tight seal, wherein the second sealing portion comprises a second pair of sealing elements that define opposed third and fourth sides of the liquid-tight seal.

6. The surgical instrument of claim 1, wherein the first and second sealing portions are configured to cooperate to define a liquid-tight seal having a first side, a second side opposed from the first side, a third side, and a fourth side opposed from the third side, wherein one of the first or second sealing portions is configured to define the first, second, and third sides, wherein the other of the first or second sealing portions is configured to define the fourth side.

7. The surgical instrument of claim 1, wherein one of the first or second sealing portions has a U shape defining an opening, and the other of the first or second sealing portions has a linear shape configured to close the opening when the shaft assembly is attached to the body assembly.

8. The surgical instrument of claim 1, wherein the second sealing portion comprises a wiper, wherein the wiper is configured to contact and wipe liquid from the first electrical contact during attachment of the shaft assembly to the body assembly.

9. The surgical instrument of claim 1, wherein the first sealing portion includes a lower opening configured to promote drainage of liquid from the first electrical contact during attachment of the shaft assembly to the body assembly.

10. The surgical instrument of claim 1, wherein at least one of the first sealing portion or the second sealing portion includes an accordion flap.

11. The surgical instrument of claim 1, wherein the first sealing portion includes a first trapezoidal feature and the second sealing portion includes a second trapezoidal feature configured to mate with the first trapezoidal feature.

12. The surgical instrument of claim 1, wherein the first sealing element circumferentially surrounds the first electrical contact, wherein the second sealing element circumferentially surrounds the second electrical contact.

13. The surgical instrument of claim 1, wherein the first sealing portion includes a first interlocking feature and the second sealing portion includes a second interlocking feature configured to interlock with the first interlocking feature when the shaft assembly is attached to the body assembly.

14. The surgical instrument of claim 1, wherein the first sealing portion includes a plurality of first teeth, wherein the second sealing portion includes a plurality of second teeth configured to sealingly engage the first teeth when the shaft assembly is attached to the body assembly.

15. A surgical instrument, comprising:
(a) a body assembly, wherein the body assembly includes a first electrical connector;
(b) a shaft assembly defining a longitudinal axis, wherein the shaft assembly is configured to slide into engagement with the body assembly along an installation axis that extends transversely to the longitudinal axis, wherein the shaft assembly includes a second electrical connector configured to establish an electrical connection with the first electrical connector when the shaft assembly attaches to the body assembly;
(c) a sealing layer disposed between the shaft assembly and the body assembly, wherein the sealing layer includes:
(i) a first sealing portion disposed on a distal portion of the body assembly, and
(ii) a second sealing portion disposed on a proximal portion of the shaft assembly,
wherein the first and second sealing portions are configured to cooperate to establish a liquid-tight seal that surrounds the electrical connection when the shaft assembly is attached to the body assembly; and
(d) an end effector at a distal end of the shaft assembly, wherein the end effector is operable to treat tissue.

16. The surgical instrument of claim 15, wherein the sealing layer defines a seal plane that extends parallel to the installation axis.

17. A surgical instrument, comprising:
(a) a body assembly, wherein the body assembly includes:
(i) a first electrical contact, and
(ii) a first sealing portion;
(b) a shaft assembly, wherein the shaft assembly is configured to releasably attach to and extend distally from the body assembly, wherein the shaft assembly includes:
(i) a second electrical contact, and
(ii) a second sealing portion; and
(c) an end effector at a distal end of the shaft assembly, wherein the end effector is operable to treat tissue,
wherein the first and second electrical contacts are configured to electrically couple together to establish an electrical connection therebetween when the shaft assembly is attached to the body assembly,
wherein the first sealing portion is configured to sealingly engage a portion of the shaft assembly and the second sealing portion is configured to sealingly engage a portion of the body assembly to thereby establish a liquid-tight seal that surrounds the electrical connection when the shaft assembly is attached to the body assembly.

18. The surgical instrument of claim 17, wherein the first and second sealing portions are configured to cooperate to define a liquid-tight seal having a first side, a second side opposed from the first side, a third side, and a fourth side opposed from the third side, wherein one of the first or second sealing portions is configured to define the first, second, and third sides, wherein the other of the first or second sealing portions is configured to define the fourth side.

* * * * *